US011865175B1

(12) United States Patent
Jordan et al.

(10) Patent No.: US 11,865,175 B1
(45) Date of Patent: Jan. 9, 2024

(54) POST-TRANSPLANTATION PROPHYLAXIS AND TREATMENTS FOR ANTIBODY-MEDIATED REJECTION OF SOLID ORGAN TRANSPLANT

(71) Applicant: Cedars-Sinai Medical Center, Los Angeles, CA (US)

(72) Inventors: Stanley Jordan, Manhattan Beach, CA (US); Ashley Vo, Northridge, CA (US); Jua Choi, Porter Ranch, CA (US)

(73) Assignee: Cedars-Sinai Medical Center, Los Angeles, CA (US)

( * ) Notice: Subject to any disclaimer, the term of this patent is extended or adjusted under 35 U.S.C. 154(b) by 473 days.

(21) Appl. No.: 15/967,034

(22) Filed: Apr. 30, 2018

Related U.S. Application Data

(60) Provisional application No. 62/491,498, filed on Apr. 28, 2017.

(51) Int. Cl.
| | |
|---|---|
| *A61K 39/395* | (2006.01) |
| *A61P 37/06* | (2006.01) |
| *C07K 14/705* | (2006.01) |
| *A61K 38/17* | (2006.01) |
| *A61K 39/00* | (2006.01) |

(52) U.S. Cl.
CPC .... *A61K 39/39541* (2013.01); *A61K 38/1774* (2013.01); *A61K 39/3955* (2013.01); *A61P 37/06* (2018.01); *C07K 14/705* (2013.01); *A61K 2039/505* (2013.01); *A61K 2039/545* (2013.01); *A61K 2300/00* (2013.01)

(58) Field of Classification Search
CPC .......... A61K 39/3955; A61K 2039/505; A61P 37/06
See application file for complete search history.

(56) References Cited

U.S. PATENT DOCUMENTS

| | | | |
|---|---|---|---|
| 11,149,091 B2 | 10/2021 | Jordan et al. | |
| 2009/0311255 A1 | 12/2009 | Brunetta et al. | |
| 2014/0314748 A1 | 10/2014 | Gokarn et al. | |
| 2016/0346387 A1 | 12/2016 | Brunetta | |
| 2020/0207864 A1 | 7/2020 | Jordan et al. | |
| 2022/0098317 A1 | 3/2022 | Jordan et al. | |

FOREIGN PATENT DOCUMENTS

| | | | |
|---|---|---|---|
| WO | 2017/004091 | * | 1/2017 |
| WO | 2017100722 A1 | | 6/2017 |

OTHER PUBLICATIONS

Loupy et al (Transplantation, 89(11):1403-1410, Jun. 15, 2010).*
Vo et al (Transplantation, 98(3):312-319, 2014).*
Shehata et al (Transfusion Mecicine Reveiws, 24(1):Suppl 1. S7-S27, 2010).*
Marfo et al (Clin. J. Am. Soc. Nephrol, 6:922-936, 2011).*
Asante-Korang et al (The Journal of Heart and Lung Transplantation, 34:175-181, 2015).*
Zachary et al, (Transplantation, 95(5):701-704, 2013).*
Fehr et al (Transplantation 87(12):1837-1841, 2009).*
Billing et al (Transplantation, 86(9):1214-1221, 2008).*
Kahwaje et al (Transplant International, 29:1276-1285, Oct. 24, 2016).*
clinical trials.gov, Phase II Study to Evaluate the Efficacy of IdeS to Desensitize Transplant Patients with Positive Crossmatch Test (HighIdeS), Mar. 30, 2017, ClinicalTrials.Gov Identifier: NCT02790437, 3 Pages.
Jordan et al., IgG Endopeptidase in Highly Sensetized Patients Undergoing Transplantation, The New England Journal of Medicine, 2017, vol. 377(5), pp. 442-453.
Jordan et al., Experience with the Bacterial Enzyme IdeS (IgG Endopeptidase) for Desensitization of Highly-HLA Sensitized (HS) Kidney Allograft Recepients, Abstract 166, 2017 American Transplant Congress, Retrieved from: [https://atcmeetingabstracts.com/abstract/experience-with-the-bacterial-enzyme-ides-igg-endopeptidase-for-desensitization-of-highly-hla-sensitized-hs-kidney-allograft-recipients/].
Jordan et al., Follow Up Patients Treated with the IgG Endopeptidase (IdeS) for Desensitization and HLA Incompatible (HLAi) Kidney Transplantation, Abstract 523, 2018 American Transplant Congress, Retrieved from: [https://atcmeetingabstracts.com/abstract/follow-up-of-patients-treated-with-the-igg-endopeptidase-ides-for-desensitization-and-hla-incompatible-hlai-kidney-transplantation/].
Vo et al., Benefits of Rituximab Combined with Intravenous Immunoglobulin for Desensitization in Kidney Transplant Recepients, Transplantation, 2014, vol. 98(3), pp. 312-319.
clinical trials.gov, Phase II Study, Evaluation of Safety and Efficacy of IdeS in Chronic Kidney Disease, V. 1, Aug. 22, 2014, Clinical Trials.Gov Identifier: NCT02224820, 7 Pages.
clinical trials.gov, Phase II Study, Evaluation of Safety and Efficacy of IdeS in Chronic Kidney Disease, V. 2, Mar. 17, 2015, Clinical Trials.Gov Identifier: NCT02224820, 6 Pages.
clinical trials.gov, Phase II Study, Evaluation of Safety and Efficacy of IdeS in Chronic Kidney Disease, V. 3, Apr. 19, 2016, Clinical Trials.Gov Identifier: NCT02224820, 15 Pages.
clinical trials.gov, Phase II Study, Evaluation of Safety and Efficacy of IdeS in Chronic Kidney Disease, V. 4, Jan. 18, 2017, Clinical Trials.Gov Identifier: NCT02224820, 2018, 15 Pages.
clinical trials.gov, Ides in Highly Sensitized Patients Awaiting Kidney Transplantation, V. 1, Apr. 24, 2015, Clinical Trials.Gov Identifier: NCT02426684, 8 Pages.
clinical trials.gov, Ides in Highly Sensitized Patients Awaiting Kidney Transplantation, V. 2, Jun. 17, 2015, Clinical Trials.Gov Identifier: NCT02426684, 8 Pages.
clinical trials.gov, Ides in Highly Sensitized Patients Awaiting Kidney Transplantation, V. 3, Oct. 7, 2016, Clinical Trials.Gov Identifier: NCT02426684, 9 Pages.

(Continued)

*Primary Examiner* — Hong Sang
(74) *Attorney, Agent, or Firm* — Nixon Peabody LLP; Linda B. Huber; Suwei Zhu

(57) ABSTRACT

Provided herein are methods for treating, inhibiting, reducing the likelihood of and/or reducing the severity of antibody-mediated rejection (ABMR) in a subject with organ transplantation, by selecting a subject that has undergone an organ transplant; and administering to the subject a therapeutically effective amount of intravenous immunoglobulin (IVIG) and an anti-CD20 agent to the subject after transplantation, or both before and after transplantation.

20 Claims, 19 Drawing Sheets

(56) References Cited

OTHER PUBLICATIONS clinical trials.gov, Ides in Highly Sensitized Patients Awaiting Kidney Transplantation, V. 4, Sep. 25, 2017, Clinical Trials.Gov Identifier: NCT02426684, 8 Pages.
clinical trials.gov, Study to Evaluate the Safety, Tolerability, Efficacy and PK of IdeS in Kidney Transplantation, V. 1, Jun. 17, 2015, Clinical Trials.Gov Identifier: NCT02475551, 7 Pages.
clinical trials.gov, Study to Evaluate the Safety, Tolerability, Efficacy and PK of IdeS in Kidney Transplantation, V. 2, Jun. 22, 2015, Clinical Trials.Gov Identifier: NCT02475551, 7 Pages.
clinical trials.gov, Study to Evaluate the Safety, Tolerability, Efficacy and PK of IdeS in Kidney Transplantation, V. 3, May 23, 2016, Clinical Trials.Gov Identifier: NCT02475551, 7 Pages.
clinical trials.gov, Study to Evaluate the Safety, Tolerability, Efficacy and PK of IdeS in Kidney Transplantation, V. 4, Sep. 7, 2016, Clinical Trials.Gov Identifier: NCT02475551, 7 Pages.
clinical trials.gov, Study to Evaluate the Safety, Tolerability, Efficacy and PK of IdeS in Kidney Transplantation, V. 5, Jan. 11, 2017, Clinical Trials.Gov Identifier: NCT02475551, 7 Pages.
clinical trials.gov, Study to Evaluate the Safety, Tolerability, Efficacy and PK of IdeS in Kidney Transplantation, V. 6, Jan. 18, 2017, Clinical Trials.Gov Identifier: NCT02475551, 7 Pages.
clinical trials.gov, Study to Evaluate the Safety, Tolerability, Efficacy and PK of IdeS in Kidney Transplantation, V. 7, Jul. 11, 2017, Clinical Trials.Gov Identifier: NCT02475551, 7 Pages.
clinical trials.gov, Study to Evaluate the Safety, Tolerability, Efficacy and PK of IdeS in Kidney Transplantation, V. 8, Jan. 5, 2018, Clinical Trials.Gov Identifier: NCT02475551, 7 Pages.
Hychko et al., A Systematic Review and Meta-Analysis of Rituximab in Antibody-Mediated Renal Allograft Rejection, Int. J. Organ Transplant Med., 2011, vol. 2(2), pp. 51-56.
Vo et al. Rituximab and Intravenous Immune Globulin for Desensitization during Renal Transplantation, The New England Journal of Medicine, 2008, vol. 359, pp. 242-251.
Vo et al. Efficacy, Outcomes, and Cost-Effectiveness of Desensitization Using IVIG and Rituximab, Transplantation, 2013, vol. 95, pp. 852-858.
Jordan et al., Imlifidase Desensitization in Crossmatch-positive, Highly Sensitized Kidney Transplant Recipients: Results of an International Phase 2 Trial (Highdes), Transplatation, 2021, vol. 105(8), pp. 1808-1817.
Choi et al., First Experience with Obinutuzumab (Type II Anti-CD20) in Patients with Treatment-Resistant Glomerular Diseases and Antibody-Mediated Rejection, Am J Transplant, 2016, vol. 16(3), Abstract Only.
Mossner et al., Increasing the Efficacy of CD20 Antibody Therapy through the Engineering of a New Type II Anti-CD20 Antibody with Enhanced Direct and Immune Effector Cell-Mediated B-cell Cytotoxicity, Blood, 2010, vol. 115(22), pp. 4393-4402.
International Search Report and Written Opinion of PCT Application No. PCT/US2016/066033, dated Mar. 3, 2017, 9 Pages.
Basu et al., Ofatumumab for Rituximab-Resistant Nephrotic Syndrome, 2014, N. Engl. J. Med, vol. 370(13), pp. 1268-1270.
Brown et al., Obinutuzumab Plus Fludarabine/Cyclophosphamide or Bendamustine in the Initial Therapy of CLL Patients: The Phase 1b GALTON Trial, 2015, Blood, vol. 125(18), pp. 2779-2785.
Goede et al., Obinutuzumab Plus Chlorambucil in Patients with CLL and Coexisting Conditions, 2014, N. Engl. J. Med., vol. 370(12), pp. 1101-1110.
Sehn et al., A Phase 1 Study of Obinutuzumab Induction Followed by 2 Years of Maintenance in Patients with Relapsed CD20-Positive B-cell Malignancies, 2012, Blood, vol. 119(22), pp. 5118-5125.
International Preliminary Report on Patentability of PCT Application No. PCT/US2016/066033, dated Jun. 12, 2018, 8 Pages.
Gulati et al., Efficacy and Safety of Treatment with Rituximab for Difficult Steroid-Resistant and Dependant Nephrotic Syndrome: Multicentric Report, Clin. J. Am. Soc. Nephro., 2010, vol. 5, pp. 2207-2212.
Smith et al., Is there a Role for Rituximab in the Treatment of Idiopathic Childhood Nephrotic Syndrome?, Pediatr Nephrol, 2007, vol. 22, pp. 893-898.
"Genentech's Gazyva (obinutuzumab), in Combination With Standard of Care, More Than Doubles the Percentage of Lupus Nephritis Patients Achieving Complete Renal Response, Compared To Standard of Care Alone" retrieved from: [https://www.gene.com/media/press-releases/14821/2019-11-09/genentechs-gazyva-obinutuzumab-in-combin], 2019.
"FDA grants Breakthrough Therapy Designation for Roche's Gazyva (obinutuzumab) in Lupus Nephritis" retrieved from: [https://www.roche.com/media/releases/med-cor-2019-09-18.htm], 2019.
Sethi et al., Obinutuzumab is Effective for the Treatment of Refractory Membranous Nephropathy, Kidney International Reports, 2020, vol. 5, pp. 1510-1531.
Segarra et al., Successful Treatment of Membranous Glomerulonephritis with Rituximab in Calcineurin Inhibitor-Dependent Patients, Clinical Journal of American Society of Nephrology, 2009, vol. 4(16), pp. 1083-1088.
Clinical Trial NCT02550652 retrieved from: [https://clinicaltrials.gov/ct2/history/NCT02550652?A=1&B=1&C=merged], first posted: Sep. 15, 2015, 12 pages.
Nozu et al., Rituximab treatment for posttransplant lymphoproliferative disorder (PTLD) induces complete remission of recurrent nephrotic syndrome, Pediatr Nephrol, 2005, vol. 20, pp. 1660-1663.

\* cited by examiner

Patient 3

Patient 4

POST-TRANSPLANTATION PROPHYLAXIS AND TREATMENTS FOR ANTIBODY-MEDIATED REJECTION OF SOLID ORGAN TRANSPLANT

CROSS-REFERENCE TO RELATED APPLICATIONS

This application includes a claim or priority under 35 U.S.C. § 119(e) to U.S. provisional patent application No. 62/491,498, filed Apr. 28, 2017, the entirety of which is hereby incorporated by reference.

FIELD OF INVENTION

Embodiments of the invention relate to treatments for antibody-mediated transplant rejection.

BACKGROUND

All publications herein are incorporated by reference to the same extent as if each individual publication or patent application was specifically and individually indicated to be incorporated by reference. The following description includes information that may be useful in understanding the present invention. It is not an admission that any of the information provided herein is prior art or relevant to the presently claimed invention, or that any publication specifically or implicitly referenced is prior art.

Antibody-mediated rejection (ABMR) is a unique, significant and often severe form of allograft rejection. While renal transplantation is considered the treatment of choice for end-stage renal disease, rates of transplantation remain low for patients with high levels of preformed anti-human leukocyte antigen (HLA) antibodies. In such cases, the immunologic barrier, linked to an increased risk of antibody-mediated rejection and poor graft survival, remains a major deterrent to transplantation. Approximately 30% of the patients on transplant waiting lists currently have evidence of sensitization in the form of alloantibodies that were generated through exposure to previous transplants, blood transfusions, pregnancy or other events. The presence of a panel-reactive antibody level of ≥80% to the loci tested for matching (i.e., highly sensitized) creates difficulty in finding matched kidneys from compatible donors and results in about one of 7 such patients receiving a kidney transplant in a given year.

Various attempts designed to improve transplant rates in highly sensitized patients incorporate the use of desensitization protocols combining B lymphocyte-depleting agents (e.g., rituximab, anti-CD20), intravenous immunoglobulin (IVIG), and plasmapheresis, combined with better stratification of immunological risk with the use of sensitive donor-specific human leukocyte antigen (HLA) antibody screening and avoidance techniques. Recent data support the life-saving benefits of desensitization and transplantation as compared to remaining on dialysis. However, current desensitization protocols often result in incomplete removal of donor-specific antibodies, rebound antibody production and an increased risk of acute and chronic antibody-mediated rejection, which are the primary cause of early graft loss and return to dialysis, with the attendant emotional consequences for the patients and financial consequences for the health care system. Currently, there are no approved drugs for desensitization and the management of donor-specific antibody-induced antibody-mediated rejection.

Therefore it is an objective of the present invention to provide compositions and methods for managing donor-specific ABMR by reducing the likelihood and/or the degree of rebound antibody production, for example, following transplantation.

SUMMARY OF THE INVENTION

Compositions and methods for treating, reducing the severity and/or likelihood of antibody-mediated rejection (ABMR) of an organ transplant in subjects that have undergone solid organ transplantation are provided. The compositions include intravenous immunoglobulin (IVIG) and an anti-CD20 agent or a B lymphocyte-depleting agent. The methods include administering to the subject with a solid organ transplant an effective amount of IVIG and an effective amount of an anti-CD20 agent or a B lymphocyte-depleting agent after transplantation. In some embodiments, the methods include administering to the subject with a solid organ transplant an effective amount of IVIG and an effective amount of an anti-CD20 agent both before and after transplantation. The IVIG and the anti-CD20 agent may be administered sequentially or simultaneously, typically within one to two weeks after transplantation.

Exemplary anti-CD20 agents include an antibody specific to CD20. In exemplary embodiments, the anti-CD20 agent includes ofatumumab, rituximab, obinutuzumab, ibritumomab, Ibritumomab tiuxetan, tositumomab, Ocaratuzumab, Ocrelizumab, TRU-015, IMMU-106 or a combination thereof.

In some embodiments, the methods for treating, reducing the severity and/or likelihood of ABMR further include selecting a subject in need of or having undergone an organ transplantation. In some aspects, the subject in need of or having undergone an organ transplantation has, or has had, donor-specific human leukocyte antigen (HLA) antibody. In some aspects, the subject is undergoing or has undergone one or more desensitization treatment before or during the organ transplantation.

Generally, the methods for treating, reducing the severity and/or likelihood of ABMR in a subject that has undergone organ transplantation by administering an effective amount of IVIG and an effective amount of an anti-CD20 agent after transplantation are characterized by significant reductions in the sum of donor-specific antibodies and/or in the highest levels of donor-specific antibodies at about 1 month, 2 months, 3 months or later after transplantation. In comparison, subjects having undergone organ transplantation but without an effective amount of the IVIG or an anti-CD20 agents after transplantation are characterized by rebound of the levels of donor-specific antibodies at about 7-14 days after transplantation, or later. The disclosed methods of administering an effective amount of IVIG and an effective amount of an anti-CD20 agent at least after transplantation are characterized by significantly reduced likelihood of rebound and/or lower levels of HLA antibodies, compared to subjects without the administration of IVIG or an anti-CD20 agent after transplantation. Exemplary significant reductions in the sum of DSA and/or in the highest levels of DSA in subjects who are administered with IVIG and an anti-CD20 agent following transplantation, refer to less than 10%, 20%, 30%, 40%, 50%, 60%, 70%, 80%, or 90% of the sum of DSA and/or the highest levels of DSA of those without IVIG or an anti-CD20 agent following transplantation; or less than 10%, 20%, 30%, 40%, 50%, 60%, 70%, 80%, or 90% of the initial sum or initial highest level of DSA of the subject prior to a desensitization treatment, which is generally conducted before or during transplantation.

BRIEF DESCRIPTION OF THE DRAWINGS

Exemplary embodiments are illustrated in referenced figures. It is intended that the embodiments and figures disclosed herein are to be considered illustrative rather than restrictive.

FIG. 4A shows levels of HLA-antibodies before and 6 hours after treatment with IdeS at a dose of 0.25 mg/kg of body weightusing Luminex class I HLA antibody LABScreen single antigen assay. Significant reductions in binding to all HLA antigens were observed. FIG. 4B shows a similar analysis of the C1q-binding HLA antibodies (results are from the C1qScreen single-antigen assay). Complete or near-complete elimination of C1q binding was observed in samples collected one hour after treatment.

FIG. 6A shows the Swedish cohort. In FIG. 6B similar data is shown in the US cohort. FIG. 6B is a comparison of each patient's highest donor specific antibodies (MFI) at pre-desensitization, 6 hours and at one month after IdeS treatment showing significant differences in donor specific antibody rebound between studies (Sweden: n=9 and US: n=12; RM 2-way ANOVA and Sidak's multiple comparison test).

FIG. 7B shows the results of the per-protocol biopsies. Low levels of immune injury were seen in the two cohorts.

DETAILED DESCRIPTION

Figure 1A:
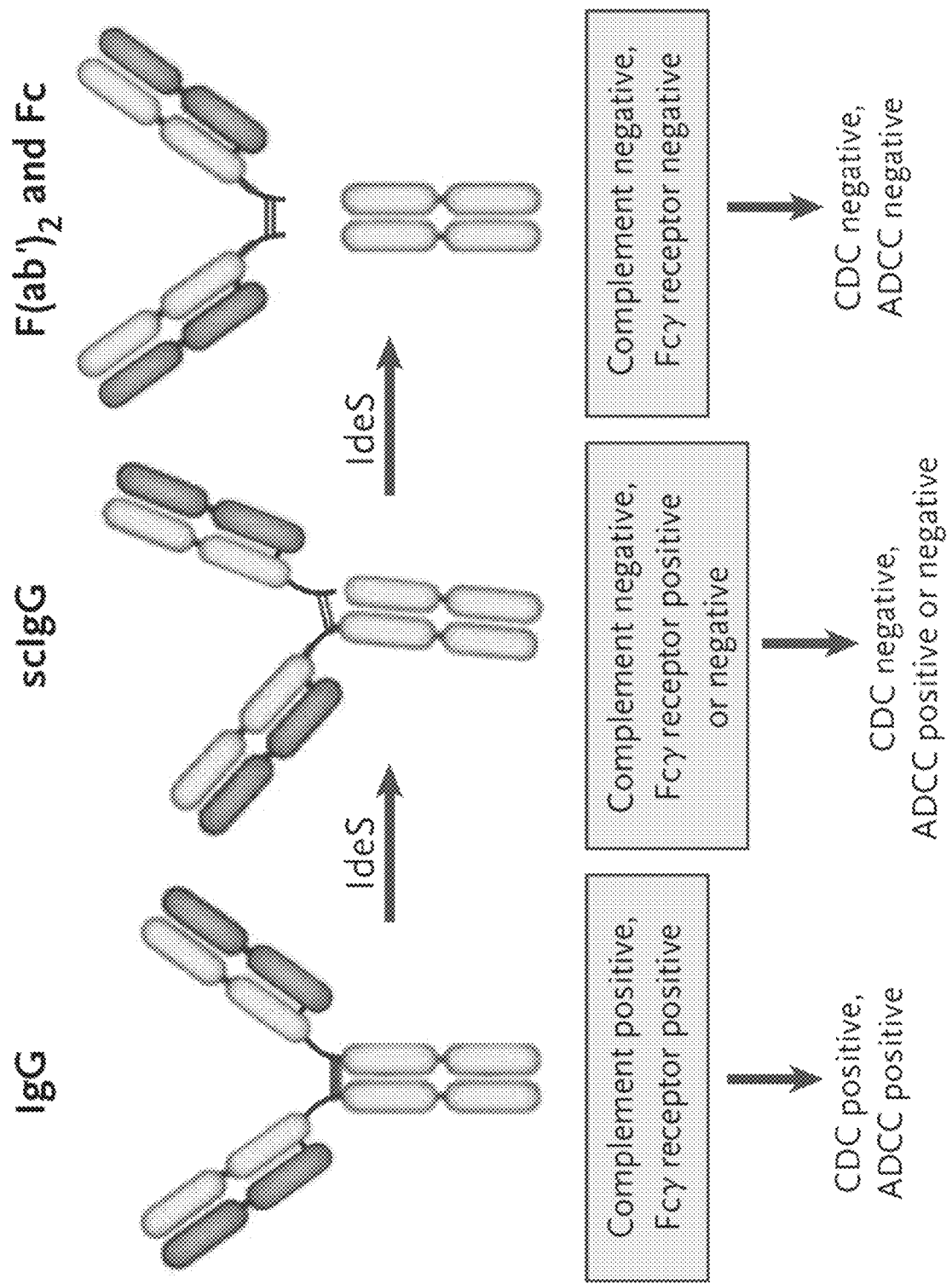
FIG. 1A depicts how IdeS cleaves intact IgG. Intact human IgG, regardless of isotype, is cleaved by IdeS in two steps. Step one results in a single cleavage of the IgG molecule (scIgG) in which one intact heavy chain remains intact. Step two then generates a fully cleaved product that cannot mediate complement dependent cytotoxicity or antibody-dependent cell-mediated cytotoxicity via Fcγ-receptors. (Prior Art)

All references cited herein are incorporated by reference in their entirety as though fully set forth. Unless defined otherwise, technical and scientific terms used herein have the same meaning as commonly understood by one of ordinary skill in the art to which this invention belongs. Allen et al., *Remington: The Science and Practice of Pharmacy* 22$^{nd}$ ed., Pharmaceutical Press (Sep. 15, 2012); Hornyak et al., *Introduction to Nanoscience and Nanotechnology*, CRC Press (2008); Singleton and Sainsbury, *Dictionary of Microbiology and Molecular Biology* 3$^{rd}$ ed., revised ed., J. Wiley & Sons (New York, NY 2006); Smith,

*March's Advanced Organic Chemistry Reactions, Mechanisms and Structure* 7th ed., J. Wiley & Sons (New York, NY 2013); Singleton, *Dictionary of DNA and Genome Technology* 3rd ed., Wiley-Blackwell (Nov. 28, 2012); and Green and Sambrook, *Molecular Cloning: A Laboratory Manual* 4th ed., Cold Spring Harbor Laboratory Press (Cold Spring Harbor, N Y 2012), provide one skilled in the art with a general guide to many of the terms used in the present application. For references on how to prepare antibodies, see Greenfield, *Antibodies A Laboratory Manual* 2nd ed., Cold Spring Harbor Press (Cold Spring Harbor NY, 2013); Köhler and Milstein, *Derivation of specific antibody-producing tissue culture and tumor lines by cell fusion*, Eur. J. Immunol. 1976 Jul., 6(7):511-9; Queen and Selick, Humanized immunoglobulins, U.S. Pat. No. 5,585,089 (1996 December); and Riechmann et al., *Reshaping human antibodies for therapy*, Nature 1988 Mar. 24, 332(6162):323-7.

One skilled in the art will recognize many methods and materials similar or equivalent to those described herein, which could be used in the practice of the present invention. Other features and advantages of the invention will become apparent from the following detailed description, taken in conjunction with the accompanying drawings, which illustrate, by way of example, various features of embodiments of the invention. Indeed, the present invention is in no way limited to the methods and materials described. For convenience, certain terms employed herein, in the specification, examples and appended claims are collected here.

Unless stated otherwise, or implicit from context, the following terms and phrases include the meanings provided below. Unless explicitly stated otherwise, or apparent from context, the terms and phrases below do not exclude the meaning that the term or phrase has acquired in the art to which it pertains. The definitions are provided to aid in describing particular embodiments, and are not intended to limit the claimed invention, because the scope of the invention is limited only by the claims. Unless otherwise defined, all technical and scientific terms used herein have the same meaning as commonly understood by one of ordinary skill in the art to which this invention belongs.

Some abbreviations used herein include: ABMR, antibody-mediated rejection; cABMR, chronic active antibody-mediated rejection; DSA, donor-specific antibody; ECD, extended criteria donor; HLA, human leukocyte antigen; PLEX, plasma exchange; SD, standard deviation.

As used herein the term "comprising" or "comprises" is used in reference to compositions, methods, and respective component(s) thereof, that are useful to an embodiment, yet open to the inclusion of unspecified elements, whether useful or not. It will be understood by those within the art that, in general, terms used herein are generally intended as "open" terms (e.g., the term "including" should be interpreted as "including but not limited to," the term "having" should be interpreted as "having at least," the term "includes" should be interpreted as "includes but is not limited to," etc.). Although the open-ended term "comprising," as a synonym of terms such as including, containing, or having, is used herein to describe and claim the invention, the present invention, or embodiments thereof, may alternatively be described using alternative terms such as "consisting of" or "consisting essentially of."

Unless stated otherwise, the terms "a" and "an" and "the" and similar references used in the context of describing a particular embodiment of the application (especially in the context of claims) can be construed to cover both the singular and the plural. The recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (for example, "such as") provided with respect to certain embodiments herein is intended merely to better illuminate the application and does not pose a limitation on the scope of the application otherwise claimed. The abbreviation, "e.g." is derived from the Latin exempli gratia, and is used herein to indicate a non-limiting example. Thus, the abbreviation "e.g." is synonymous with the term "for example." No language in the specification should be construed as indicating any non-claimed element essential to the practice of the application.

The term "sample" or "biological sample" as used herein denotes a sample taken or isolated from a biological organism, e.g., a fluid sample from a subject. Exemplary biological samples include, but are not limited to, cheek swab; mucus; whole blood, blood, serum; plasma; urine; saliva; semen; lymph; fecal extract; sputum; other body fluid or biofluid; cell sample; tissue sample (e.g., renal tissue sample); tumor sample; and/or tumor biopsy etc. The term also includes a mixture of the above-mentioned samples. The term "sample" also includes untreated or pretreated (or pre-processed) biological samples. In some embodiments, a sample can comprise one or more cells from the subject.

The term "statistically significant" or "significantly" refers to statistical evidence that there is a difference. It is defined as the probability of making a decision to reject the null hypothesis when the null hypothesis is actually true. The decision is often made using the p-value.

"Mammal" as used herein refers to any member of the class Mammalia, including, without limitation, humans and nonhuman primates such as chimpanzees and other apes and monkey species; farm animals such as cattle, sheep, pigs, goats and horses; domestic mammals such as dogs and cats; laboratory animals including rodents such as mice, rats and guinea pigs, and the like. The term does not denote a particular age or sex. Thus, adult and newborn subjects, as well as fetuses, whether male or female, are intended to be included within the scope of this term.

As used herein, a "subject" means a human or animal. Usually the animal is a vertebrate such as a primate, rodent, domestic animal or game animal. Primates include chimpanzees, cynomologous monkeys, spider monkeys, and macaques, e.g., Rhesus. Rodents include mice, rats, woodchucks, ferrets, rabbits and hamsters. Domestic and game animals include cows, horses, pigs, deer, bison, buffalo, feline species, e.g., domestic cat, and canine species, e.g., dog, fox, wolf. The terms, "patient", "individual" and "subject" are used interchangeably herein. In an embodiment, the subject is mammal. The mammal can be a human, non-human primate, mouse, rat, dog, cat, horse, or cow, but are not limited to these examples. In addition, the methods described herein can be used to treat domesticated animals and/or pets.

A subject can be one who has been previously diagnosed with or identified as having a risk of suffering from a condition in need of treatment (e.g., risk of developing ABMR after organ transplant), a risk of having a condition in need of treatment, suffering from or having a condition in need of treatment (e.g., ABMR) or one or more complications related to the condition, and optionally, have already undergone treatment for the condition or the one or more complications related to the condition. Alternatively, a subject can also be one who has not been previously diagnosed as having a condition or one or more complications related to the condition. For example, a subject can be one who exhibits one or more risk factors for a condition or one or more complications related to the condition or a subject who does not exhibit risk factors. For example, a subject can be one who exhibits one or more symptoms for a condition or one or more complications related to the condition or a subject who does not exhibit symptoms. A "subject in need" of diagnosis or treatment for a particular condition can be a subject suspected of having that condition, diagnosed as having that condition, already treated or being treated for that condition, not treated for that condition, or at risk of developing that condition. In particular embodiments, the subject is one who has renal disease, who has end-stage renal disease, or who is undergoing dialysis.

As used herein, the terms "treat," "treatment," "treating," or "amelioration" refer to therapeutic treatments, wherein the object is to reverse, alleviate, ameliorate, inhibit, slow down or stop the progression or severity of a condition associated with, a disease or disorder. The term "treating" includes reducing or alleviating at least one adverse effect or symptom of a condition, disease or disorder, such as ABMR. Treatment is generally "effective" if one or more symptoms or clinical markers are reduced. Alternatively, treatment is "effective" if the progression of a disease is reduced or halted. That is, "treatment" includes not just the improvement of symptoms or markers, but also a cessation of at least slowing of progress or worsening of symptoms that would be expected in absence of treatment. Beneficial or desired clinical results include, but are not limited to, alleviation of one or more symptom(s), diminishment of extent of disease, stabilized (i.e., not worsening) state of disease, delay or slowing of disease progression, amelioration or palliation of the disease state, and remission (whether partial or total), whether detectable or undetectable. The term "treatment" of a disease also includes providing relief from the symptoms or side-effects of the disease (including palliative treatment).

"Beneficial results" or "desired results" may include, but are in no way limited to, lessening or alleviating the severity of the disease condition, preventing the disease condition from worsening, curing the disease condition, preventing the disease condition from developing, lowering the chances of a patient developing the disease condition, decreasing morbidity and mortality, and prolonging a patient's life or life expectancy. As non-limiting examples, "beneficial results" or "desired results" may be alleviation of one or more symptom(s), diminishment of extent of the deficit, stabilized (i.e., not worsening) state of cancer progression, delay or slowing of metastasis or invasiveness, and amelioration or palliation of symptoms associated with the cancer.

As used herein, the term "administering," refers to the placement an agent as disclosed herein into a subject by a method or route which results in at least partial localization of the agents at a desired site As used herein, the term "antibody" refers to an intact immunoglobulin or to a monoclonal or polyclonal antigen-binding fragment with the Fc (crystallizable fragment) region or FcRn binding fragment of the Fc region, referred to herein as the "Fe fragment" or "Fe domain". Antigen-binding fragments may be produced by recombinant DNA techniques or by enzymatic or chemical cleavage of intact antibodies. Antigen-binding fragments include, inter alia, Fab, Fab', F(ab')$_2$, Fv, dAb, and complementarity determining region (CDR) fragments, single-chain antibodies (scFv), single domain antibodies, chimeric antibodies, diabodies and polypeptides that contain at least a portion of an immunoglobulin that is sufficient to confer specific antigen binding to the polypeptide. The Fc domain includes portions of two heavy chains contributing to two or three classes of the antibody. The Fc domain may be produced by recombinant DNA techniques or by enzymatic (e.g. papain cleavage) or via chemical cleavage of intact antibodies.

The term "antibody fragment," as used herein, refer to a protein fragment that comprises only a portion of an intact antibody, generally including an antigen binding site of the intact antibody and thus retaining the ability to bind antigen. Examples of antibody fragments encompassed by the present definition include: (i) the Fab fragment, having VL, CL, VH and CH1 domains; (ii) the Fab" fragment, which is a Fab fragment having one or more cysteine residues at the C-terminus of the CH1 domain; (iii) the Fd fragment having VH and CH1 domains; (iv) the Fd' fragment having VH and CH1 domains and one or more cysteine residues at the C-terminus of the CH1 domain; (v) the Fv fragment having the VL and VH domains of a single arm of an antibody; (vi) the dAb fragment (Ward et al., Nature 341, 544-546 (1989)) which consists of a VH domain; (vii) isolated CDR regions; (viii) F(ab')$_2$ fragments, a bivalent fragment including two Fab' fragments linked by a disulphide bridge at the hinge region; (ix) single chain antibody molecules (e.g., single chain Fv; scFv) (Bird et al., Science 242:423-426 (1988); and Huston et al., PNAS (USA) 85:5879-5883 (1988)); (x) "diabodies" with two antigen binding sites, comprising a heavy chain variable domain (VH) connected to a light chain variable domain (VL) in the same polypeptide chain (see, e.g., EP 404,097; WO 93/11161; and Hollinger et al., Proc. Natl. Acad. Sci. USA, 90:6444-6448 (1993)); (xi) "linear antibodies" comprising a pair of tandem Fd segments (VH-CH1-VH-CH1) which, together with complementary light chain polypeptides, form a pair of antigen binding regions (Zapata et al. Protein Eng. 8(10):1057-1062 (1995); and U.S. Pat. No. 5,641,870).

As used herein, "selectively binds" or "specifically binds" refers to the ability of an antibody or antibody fragment thereof described herein to bind to a target, such as a molecule present on the cell-surface, with a KD $10^{-5}$ M (10000 nM) or less, e.g., $10^{-6}$ M, $10^{-7}$ M, $10^{-8}$ M, $10^{-9}$ M, $10^{-10}$ M, $10^{-11}$ M, $10^{-12}$ M, or less. Specific binding can be influenced by, for example, the affinity and avidity of the polypeptide agent and the concentration of polypeptide agent. The person of ordinary skill in the art can determine appropriate conditions under which the polypeptide agents described herein selectively bind the targets using any suitable methods, such as titration of a polypeptide agent in a suitable cell binding assay.

As used herein, "ineffective" treatment refers to when a subject is administered a treatment and there is less than 1%, 5%, 10%, 15%, 20%, or 25% improvement in symptoms. In exemplary embodiments, standard-of-care treatment for kidney transplant is ineffective if there is less than 1%, 5%, 10%, 15%, 20%, or 25% improvement in ABMR, for example only about 20%-25% improvement in ABMR.

The term "effective amount" refers to the amount of an agent that decreases at least one or more symptom of the disease or disorder, and relates to a sufficient amount of pharmacological composition to provide the desired effect. The phrase "therapeutically effective amount" means a sufficient amount of the composition to treat a disorder, at a reasonable benefit/risk ratio applicable to any medical treatment. In one embodiment, the pharmaceutical (therapeutic) composition comprises, consists of or consists essentially of an anti-CD20 agent. In another embodiment, the pharmaceutical (therapeutic) composition comprises, consists of or consists essentially of IVIG. A therapeutically or prophylactically significant reduction in a symptom is, e.g. at least about 25%, at least about 30%, at least about 40%, at least about 50%, at least about 60%, at least about 70%, at least about 80%, at least about 90%, at least about 100%, at least about 125%, at least about 150% or more in a measured parameter as compared to a control or non-treated subject or the state of the subject prior to administering the IVIG and anti-CD20 agent. Measured or measurable parameters include clinically detectable markers of disease, for example, elevated or depressed levels of a biological marker, as well as parameters related to a clinically accepted scale of symptoms or markers for fibrosis and/or inflammation. It will be understood, however, that the total daily usage of the compositions and formulations as disclosed herein will be decided by the attending physician within the scope of sound medical judgment. The exact amount required will vary depending on factors such as the type of disease being treated, gender, age, and weight of the subject.

Provided herein are methods for treating, inhibiting, reducing the likelihood of and/or reduce severity of antibody mediated rejection of an organ transplant in a subject in need thereof, wherein the subject has undergone organ transplant. The methods comprise, consist of or consist essentially of administering to the subject that has undergone an organ transplant, therapeutically effective amounts of intravenous immunoglobulin (IVIG) and an anti-CD20 agent. In an embodiment, the IVIG and the anti-CD20 agent are administered to the subject after transplantation. Accordingly, the methods may include first selecting a subject that has undergone an organ transplant, prior to administration. In another embodiment, the IVIG and the anti-CD20 agent are administered to the subject both before and after transplantation. In an embodiment, the IVIG and the anti-CD20 agent are administered sequentially. In an embodiment, the IVIG and the anti-CD20 agent are administered are administered simultaneously. In one embodiment, the subject has undergone treatment for depletion for anti-HLA donor-specific antibodies (DSA). In another embodiment, the subject is undergoing treatment for depletion for anti-HLA donor-specific antibodies (DSA).

Also provided herein are methods for reducing and/or eliminating donor specific HLA antibodies in a subject that undergone organ transplant in a subject in need thereof. The methods comprise, consist of or consist essentially of administering to the subject that has undergone an organ transplant, therapeutically effective amounts of intravenous immunoglobulin (IVIG) and an anti-CD20 agent. In an embodiment, the IVIG and anti-CD20 agent are administered after transplantation. Accordingly, the methods may include first selecting a subject that has undergone an organ transplant, prior to administration. In an embodiment, the IVIG and the anti-CD20 agent are administered sequentially. In an embodiment, the IVIG and the anti-CD20 agent are administered simultaneously. In one embodiment, the subject has undergone treatment for depletion for anti-HLA donor-specific antibodies (DSA). In another embodiment, the subject is undergoing treatment for depletion for anti-HLA donor-specific antibodies (DSA).

Further provided herein are methods for treating, inhibiting and/or reducing the severity of ABMR post-organ transplant in highly HLA-sensitized patients. The methods comprise, consist of or consist essentially of administering to the subject that has undergone an organ transplant, therapeutically effective amounts of intravenous immunoglobulin (IVIG) and an anti-CD20 agent. In an embodiment, the IVIG and the anti-CD20 agent are administered after transplantation. Accordingly, the methods may include first selecting a subject that has undergone an organ transplant, prior to administration. In an embodiment, the IVIG and anti-CD20 agent are administered sequentially. In an embodiment, the IVIG and anti-CD20 agent are administered are administered simultaneously. In one embodiment, the subject has undergone treatment for depletion for anti-HLA donor-specific antibodies (DSA). In another embodiment, the subject is undergoing treatment for depletion for anti-HLA donor-specific antibodies (DSA).

In various embodiments of the methods described herein, the DSAs in the subject are pre-existing or produced de novo in the patient.

In various embodiments of the methods described herein, the subject has undergone any one or more of plasmapheresis (PLEX), immune-absorption therapy or treatment with IgG degrading enzyme so as to deplete the population of DSAs.

In some embodiments, the subject has undergone transplantation of any of heart, liver, lungs, pancreas or intestines. In one embodiment, the subject has undergone kidney transplantation.

In various embodiments of the methods described herein, the anti-CD20 agent is a CD20 inhibitor. In some embodiments, the CD20 inhibitor is directly inhibits CD20. In some embodiments, the CD20 inhibitor indirectly inhibits CD20. In some embodiments, the CD20 inhibitor is a small molecule, a peptide, an antibody or a fragment thereof that specifically binds CD20, a CD20 specific antisense oligonucleotide or a nucleic acid molecule.

In one embodiment, the CD20 inhibitor is an antibody specific to CD20. In some embodiments, the anti-CD20 agent is a CD20 specific monoclonal antibody. In exemplary embodiments, the anti-CD20 agent is ofatumumab, rituximab, obinutuzumab, ibritumomab, Ibritumomab tiuxetan, tositumomab, Ocaratuzumab, Ocrelizumab, TRU-015, IMMU-106 or combinations thereof.

In various embodiments, the IVIG and the anti-CD20 agent are administered 1 day, 2 days, 3 days, 4 days, 5 days, 6 days, 7 days, 8 days, 9 day, 10 days, 11 days, 12 days, 13 days, and/or 14 days after transplantation. In some embodiments, the IVIG and the anti-CD20 agent are administered within 7 days after transplantation.

In various embodiments, the IVIG and the anti-CD20 agent are administered for about 1 month, about 2 months, about 3 months, about 4 months, about 5 months, about 6 months, about 7 months, about 8 months, about 9 months, about 10 months, about 11 months, about 12 months, about 13 months, about 14 months, about 15 months, about 16 months, about 17 months, about 18 months, about 24 months, about 30 months, or about 36 months.

In some embodiments, the anti-CD20 antibody is administered at a dose between about 100 mg/m2 and 375 mg/m2 of body surface area for a subject or a total of 1 gram for one to two doses.

In some embodiments, the effective amount of the anti-CD20 antibody is about 0.01-0.05 mg/kg/day, 0.05-0.1 mg/kg/day, 0.1 to 0.5 mg/kg/day, 0.5 to 1 mg/kg/day, 1 to 2 mg/kg/day, 2 to 3 mg/kg/day, 3 to 4 mg/kg/day, 0.5 to 5 mg/kg/day, 1 to 5 mg/kg/day, 3 to 5 mg/kg/day, 5 to 10 mg/kg/day, 10 to 20 mg/kg/day, 20 to 50 mg/kg/day, 50 to 100 mg/kg/day, 100 to 200 mg/kg/day, 200 to 300 mg/kg/day, 300 to 400 mg/kg/day, 400 to 500 mg/kg/day, 500 to 600 mg/kg/day, 600 to 700 mg/kg/day, 700 to 800 mg/kg/day, 800 to 900 mg/kg/day or 900 to 1000 mg/kg/day. In some embodiments, the anti-CD20 antibody is administered to the subject 1-3 times per day or 1-7 times per week. In some embodiments, the anti-CD20 antibody is administered to the subject for 1-5 days, 1-5 weeks, 1-5 months, or 1-5 years.

In some embodiments of the invention, the effective amounts of the anti-CD20 antibody can be in the range of about 10-50 mg/day, 50-100 mg/day, 100-150 mg/day, 150-200 mg/day, 100-200 mg/day, 200-300 mg/day, 300-400 mg/day, 400-500 mg/day, 500-600 mg/day, 600-700 mg/day, 700-800 mg/day, 800-900 mg/day, 900-1000 mg/day, 1000-1100 mg/day, 1100-1200 mg/day, 1200-1300 mg/day, 1300-1400 mg/day, 1400-1500 mg/day, 1500-1600 mg/day, 1600-1700 mg/day, 1700-1800 mg/day, 1800-1900 mg/day, 1900-2000 mg/day, 2000-2100 mg/day, 2100-2200 mg/day, 2200-2300 mg/day, 2300-2400 mg/day, 2400-2500 mg/day, 2500-2600 mg/day, 2600-2700 mg/day, 2700-2800 mg/day, 2800-2900 mg/day or 2900-3000 mg/day.

In further embodiments of the invention, the effective amount of the anti-CD20 antibody for use with the claimed methods may be in the range of 1-5 mg/kg, 5-10 mg/kg, 10-50 mg/kg, 50-100 mg/kg, 100-150 mg/kg, 150-200 mg/kg, 100-200 mg/kg, 200-300 mg/kg, 300-400 mg/kg, 400-500 mg/kg, 500-600 mg/kg, 600-700 mg/kg, 700-800 mg/kg, 800-900 mg/kg or 900-1000 mg/kg.

In some embodiments, the anti-CD20 agent is administered in dosage ranges of about 375 mg/m$^2$×body surface area to about 1000 mg/m$^2$×body surface area for 10-14 days post-transplant. The anti-CD20 agent may be administered intravenously.

In some embodiments, IVIG dosage is about 1 g/kg (max dose for >70 kg=70 g) daily×2 days or a total of 2 g/kg (max 140 g for >70 kg) over two days. IVIG may be administered intravenously or subcutaneous. In some embodiments, the effective amount of IVIG is between about 2 grams/kg and 140 grams/kg of the subject over two days.

Typical dosages of an effective amount of an anti-CD20 antibody can be in the ranges recommended by the manufacturer where known therapeutic compounds are used, and also as indicated to the skilled artisan by the in vitro responses or responses in animal models. For example, Obinutuzumab is currently recommended for the treatment of chronic lymphocytic anemia as administering 100 mg on day 1, 900 mg on day 2 and 1000 mg on day 8, and day 15. The same or similar dosing can be used in accordance with various embodiments of the present invention, or an alternate dosage may be used in connection with alternate embodiments of the invention. The actual dosage can depend upon the judgment of the physician, the condition of the patient, and the effectiveness of the therapeutic method based, for example, on the in vitro responsiveness of relevant cultured cells or histocultured tissue sample, or the responses observed in the appropriate animal models.

EXAMPLES

The following examples are not intended to limit the scope of the claims to the invention, but are rather intended to be exemplary of certain embodiments. Any variations in the exemplified methods which occur to the skilled artisan are intended to fall within the scope of the present invention.

Example 1: Experimental Methods

Patients and Study Design

The present report combines two separate open label, single arm Phase I/II studies investigating the safety and efficacy of IdeS to reduce or remove pathogenic donor specific antibodies to allow incompatible kidney transplantation. Studies were performed independently at Cedars-Sinai Medical Center, Los Angeles and at in Sweden at Uppsala University, Uppsala, Sweden and at Karolinska Institute, Stockholm. Protocols were approved by each site by an institutional review board (IRB) or ethics committee (see below), and all patients provided written, informed consent. Protocols are found at NEJM.org.

An initial dose-finding study examined the efficacy of IdeS to remove HLA antibodies in highly-HLA sensitized patients (NCT02224820). Two subsequent studies, one in the U.S. (NCT02426684) and one in Sweden (NCT02475551), reported here, examined the effectiveness, safety and tolerability of the streptococcal IgG endopeptidase IdeS given prior to kidney transplantation in highly sensitized patients to reduce or eliminate donor specific antibodies and to allow incompatible transplantation without early antibody rejection.

Eligible patients were 18 to 70 years with end-stage renal disease (ESRD) on dialysis awaiting kidney transplantation on the United Network for Organ Sharing (UNOS) (U.S.) wait list, or the Scandia Transplant list (SE). All patients exhibited extensive sensitization with a median calculated panel-reactive antibody of 95% (range 22-100%) and had a clinically significant sensitization history. Patient selection was based on levels of sensitization and wait time that had been so long as to include frequent offers of transplants obtained from deceased donor (DD) that had resulted in positive cross-matches and donor-specific antibodies that had previously prohibited transplantation. All patients provided written, informed consent.

Acceptance criteria for HLA-incompatible organs for U.S. recipients were previously reported and, briefly included a negative complement-cytotoxicity cross-match, a negative flow-cytometric cross-match, or a positive T-cell and B-cell flow-cytometric cross-match with approximately 250 channel shifts or less and usually donor specific antibody positivity. (Channel shift refers to a method of measuring the intensity of light signals generated from dye-specific fluorescent-labeled antibodies binding to HLA antigens on target cells. Light signals are converted by an analogue-to-digital converter so signals can be processed by a binary computer. The intensity of the binding is measured as degrees of channel shifts relative to negative controls.) In Sweden, patients were eligible if they had had ≥two anti-HLA antibodies with mean fluorescent intensity ≥3000. Eight patients participated in the dose-finding study, which did not include transplantation and was used to establish doses of IdeS to be used in the transplantation trials. A total of 25 patients met the criteria outlined above (14 U.S., 11 Sweden) and participated in the transplantation studies.

Donor-specific antibodies were detected using solid-phase assay systems that were currently in use at the HLA laboratory of each hospital. After safety assessments, the patients proceeded to receive a transplant from an incompatible donor. Study patients who received a kidney transplant had samples obtained before IdeS treatment for the assessment of donor-specific antibodies and flow-cytometric cross-matching and also underwent studies after treatment that included monitoring for efficacy of IgG cleavage at prespecified time points.

Patients who underwent transplantation received IdeS at a dose of 0.24 mg/kg of body weight (in the U.S.), or at a dose of 0.25 mg/kg or 0.5 mg/kg (in Sweden; both doses were investigated in a dose-finding study). IdeS was administered intravenously on day 0, usually four to 6 hours before transplantation. Cross-match and donor-specific antibody tests were conducted at 6 and 24 hours and on days 7, 30, 60, 90 (only in the U.S. study), and 180 (only in the U.S. study) after treatment to determine the efficacy of IdeS. Patients in the Swedish cohort received induction with horse antithymocyte globulin (ATGRAIVI®) for 4 days after transplantation. Patients in the U.S. cohort received induction with alemtuzumab at a dose of 30 mg administered subcutaneously 4 days post-transplant. Patients in the U.S. and Swedish studies continued to receive standard immunosuppression (i.e., prednisone (2 mg per kilogram, with a rapid tapering to 5 mg per day by 2 weeks after transplantation), mycophenolate mofetil (500 mg twice daily), and tacrolimus administered to maintain a target blood level of 7 to 9 ng per milliliter for the first 3 months, 6 to 8 ng per milliliter for months 3 to 6, and 5 to 7 ng per milliliter after 6 months): the levels of tacrolimus in blood were maintained at 10-12 ng/ml (SE) and at 8-10 ng/ml (US).

Figure 1B:
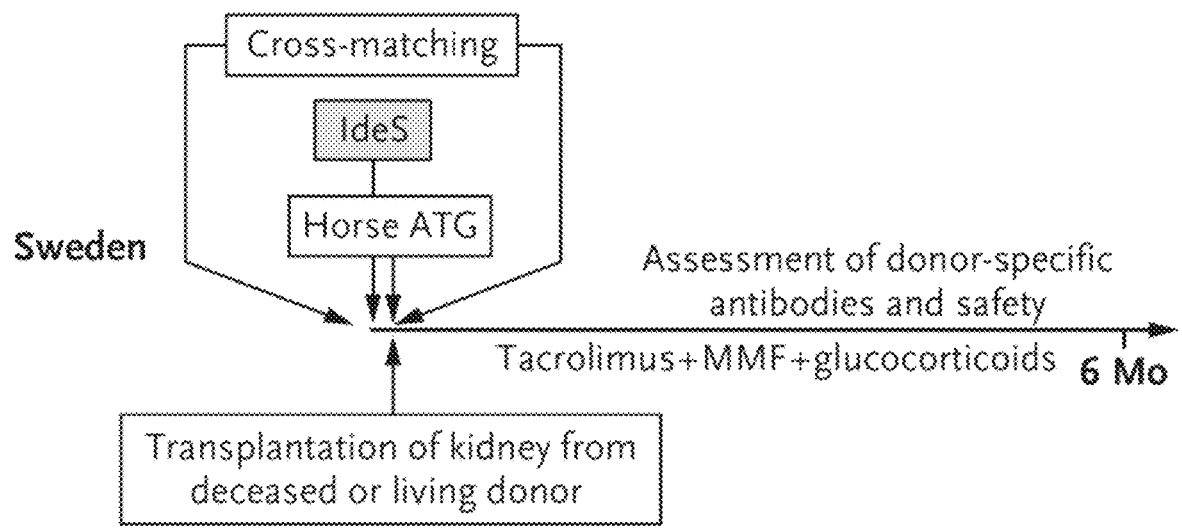
FIGS. 1B and 1C are flow diagrams of the immunosuppressive regimens at pre- and post-transplant used in the Swedish study (1B; NCT: 02475551) and the US study (1C; NCT: 02426684). A total of 12 of 14 patients in the U.S. study received desensitization with immune globulin and rituximab before transplantation. All the patients received these agents after transplantation to prevent antibody rebound. ATG denotes antithymocyte globulin, and MMF mycophenolate mofetil.
Figure 1C:
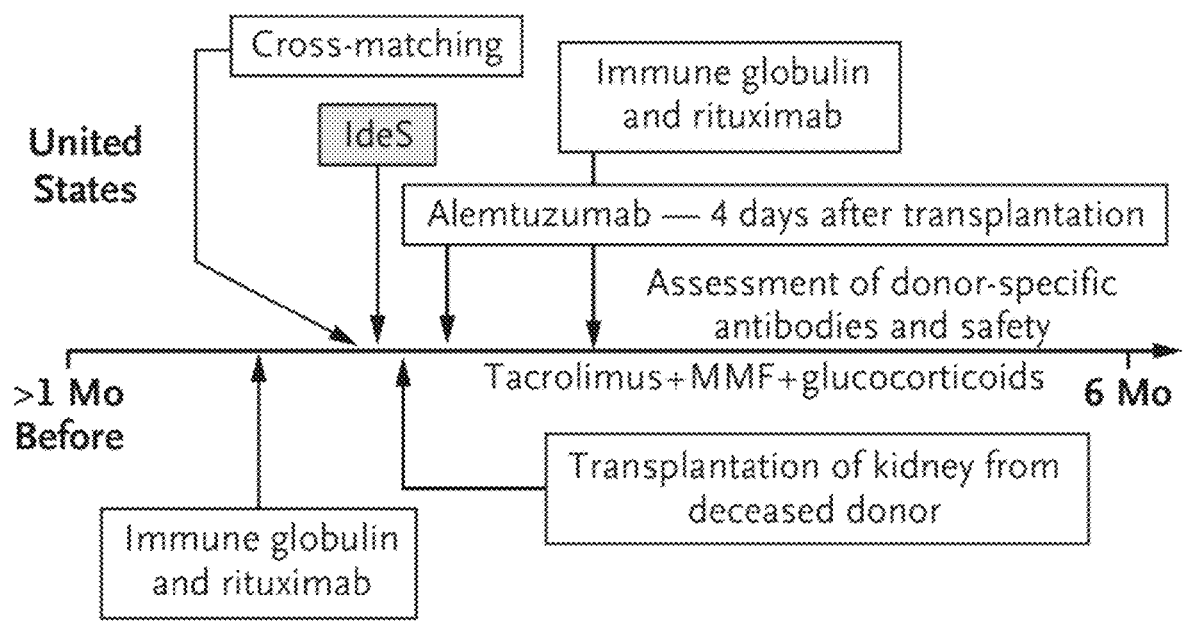
Figures 2A, 2B:
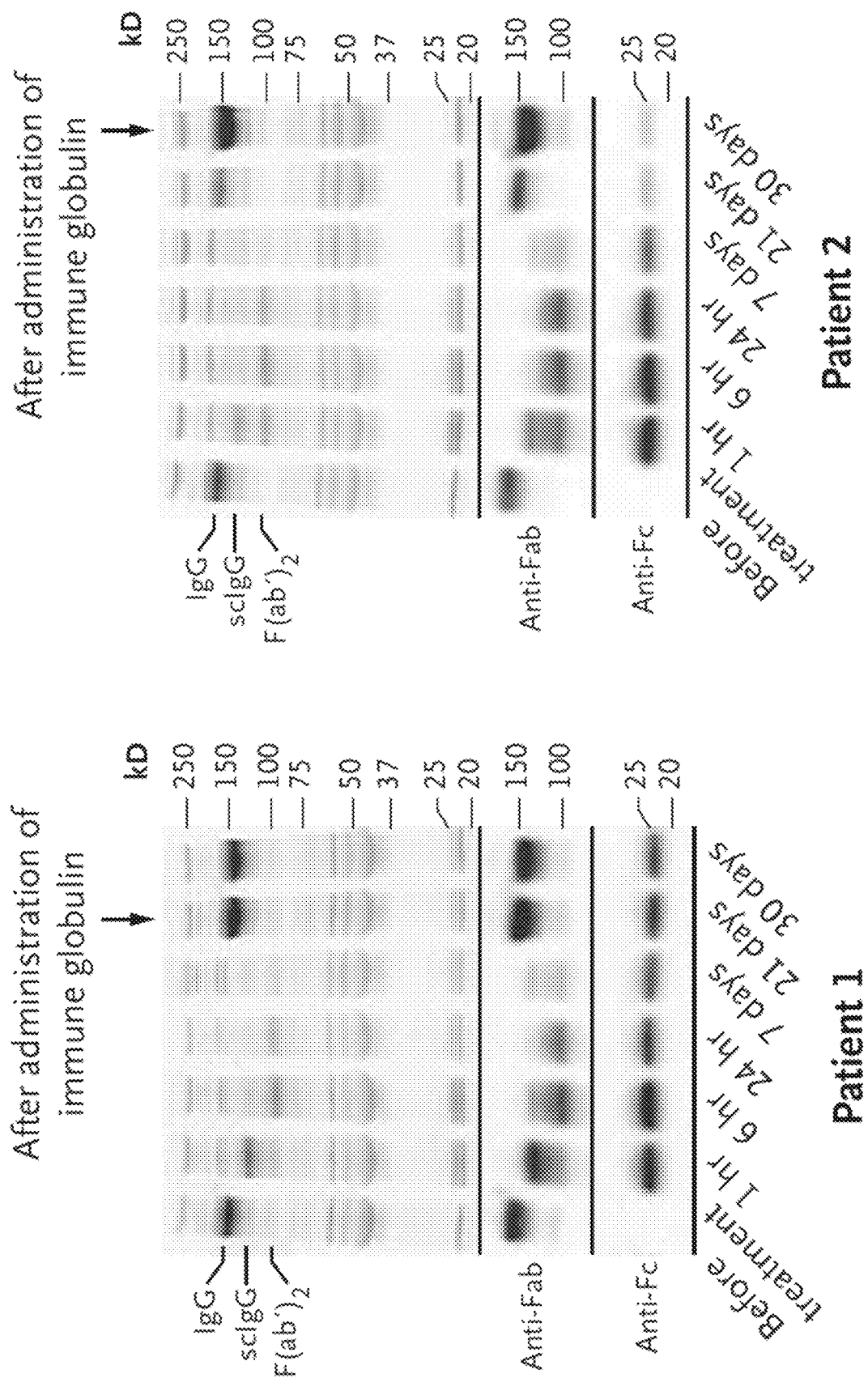
FIGS. 2A-2D show the results on serum samples from four IdeS treated patients, each respectively. Samples were collected before and at the indicated time points after IdeS treatment and subjected to SDS-PAGE (top), Western blot with Fab-specific reagent (middle) and Western blot with Fc-specific reagent (bottom). The data showed that at one hour IgG is cleaved into scIgG and F(ab')$_2$/Fc with no intact IgG remaining. At 6 hours IgG is completely cleaved into F(ab')$_2$ and Fc.
Figures 2C, 2D:
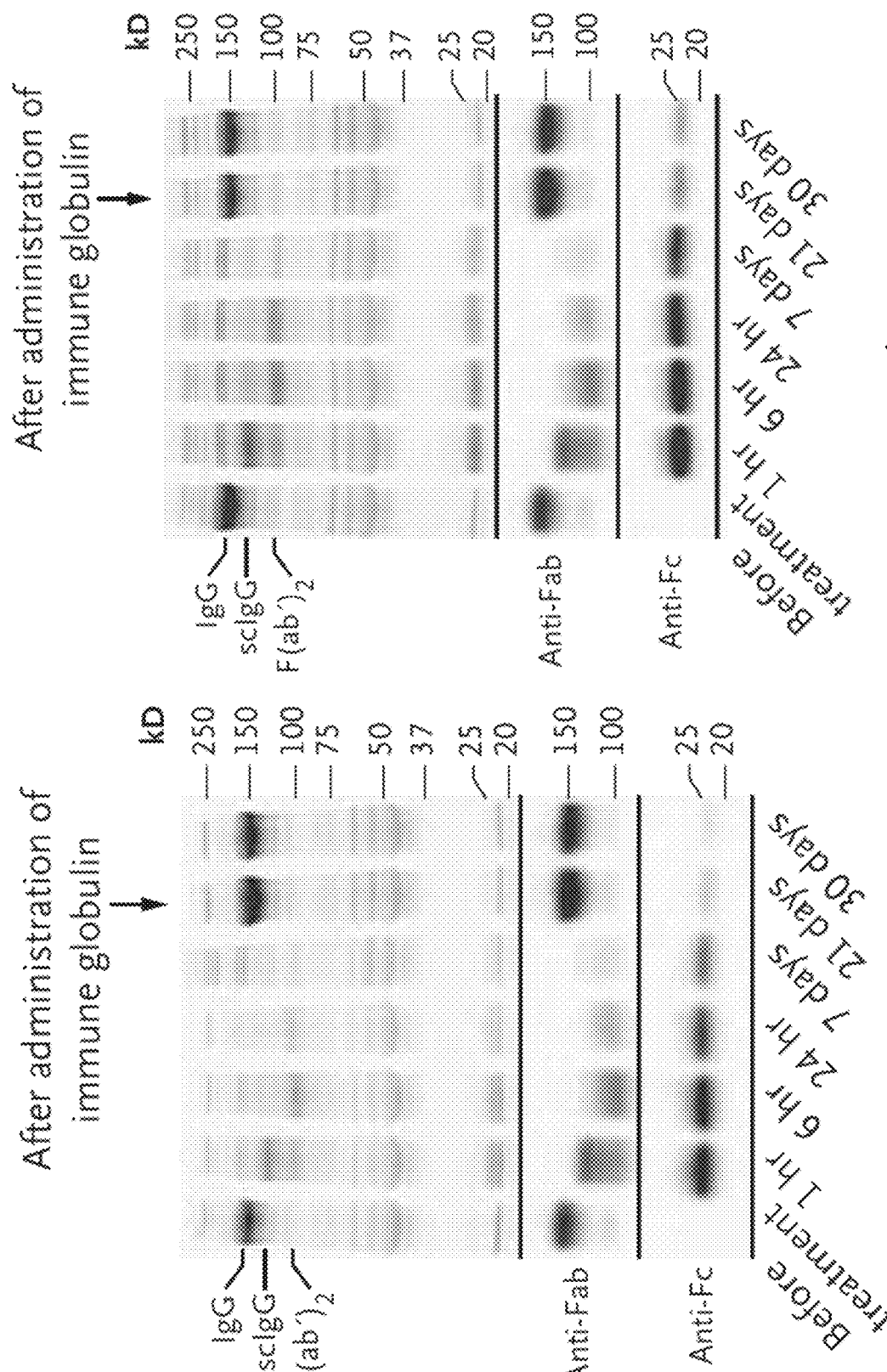

All the patients received prophylactic antibiotics to prevent bacterial infections in the absence of IgG antibodies. Patients in the U.S. study received IVIg at a dose of 2 g/kg (maximum dose 140 g) on days 7 to 14 after transplantation. Patients in the U.S. study who did not receive rituximab before kidney transplantation received rituximab at a dose of 375 mg/m$^2$ of body-surface area on days 14 to 21 after transplantation. A summary of the treatment protocols is show in FIGS. 1B and 1C. Humanized monoclonal antibodies and IVIG were administered beyond the half-life of IdeS in order to avoid digestion.

Renal-allograft biopsies were performed to assess for antibody-mediated rejection when allograft dysfunction was noted. In addition, per-protocol biopsies were performed at 6 months in the two studies. Assessments in the two studies included C4d staining with the use of the Banff 2013 criteria. A condensed version of the pathologic criteria for the assessment of antibody-mediated rejection according to the Banff 2013 is shown below.

Summary of Banff 2013 Criteria For Diagnosing Antibody Mediated Rejection in Kidney Allografts:
Banff 2013 Classification of Antibody-Mediated Rejection (ABMR) in Renal Allografts
Acute/Active ABMR; all 3 features must be present for diagnosis
1. Histologic evidence of acute tissue injury, including one or more of the following:
    Microvascular inflammation (g>0$^a$ and/or ptc >0)
    Intimal or transmural arteritis (v>0)
    Acute thrombotic microangiopathy, in the absence of any other cause
    Acute tubular injury, in the absence of any other apparent cause
2. Evidence of current/recent antibody interaction with vascular endothelium, including at least one of the following:
    Linear C4d staining in peritubular capillaries (C4d2 or C4d3 by IF on frozen sections, or C4d>0 by IHC on paraffin sections)
    At least moderate microvascular inflammation ([g+ptc] ≥2)$^b$
    Increased expression of gene transcripts in the biopsy tissue indicative of endothelial injury, if thoroughly validated
3. Serologic evidence of donor-specific antibodies (HLA or other antigens)

Chronic, Active ABMR; all Three Features Must be Present for Diagnosis
1. Morphologic evidence of chronic tissue injury, including 1 or more of the following:
    Transplant glomerulopathy (cg>0)$^c$, if no evidence of chronic TMA
    Severe peritubular capillary basement membrane multilayering (requires EM)$^d$
    Arterial intimal fibrosis of new onset, excluding other causes
2. Evidence of current/recent antibody interaction with vascular endothelium, including as least one of the following:
    Linear C4d staining in peritubular capillaries (C4d2 or C4d3 by IF on frozen sections, or C4d>0 by IHC on paraffin sections)
    At least moderate microvascular inflammation ([g+ptc] ≥2)$^b$
    Increased expression of gene transcripts in the biopsy tissue indicative of endothelial injury, if thoroughly validated
3. Serologic evidence of donor-specific antibodies (HLA or other antigens)

Banff 2013 Classification of Antibody-Mediated Rejection (ABMR) in Renal Allografts
(Footnotes)
$^a$ Recurrent/de novo glomerulonephritis should be excluded
$^b$ In the presence acute T cell-mediated rejection, borderline infiltrates, or evidence of infection, ptc≥2 alone is not sufficient to define moderate microvascular inflammation and g must be ≥1.
$^c$ Includes GBM duplication by electron microscopy only (cg1a) or GBM double contours by light microscopy
$^d$ ≥7 layers in 1 cortical peritubular capillary and ≥5 in 2 additional capillaries, avoiding portions cut tangentially Clinical Assessment Assessments included routine laboratory tests, measurement of panel-reactive antibodies and donor-specific antibodies, assessment of vital signs, and the collection of data related to adverse events (AE) and serious adverse events (SAE). All the AEs and SAEs were recorded, graded, and reported to the Institutional Review Boards (IRB) at each center, to the study sponsor, and to regulatory authorities. Samples for the analysis of IdeS levels and qualitative analysis of patients' IgG levels were assessed with the use of SDS-PAGE. IdeS cleavage and clearance of the Fc and F(ab')$_2$ fragments were analyzed using ELISA methods as previously described.

The sodium dodecyl sulfate polyacrylamide gel electrophoresis (SDS-PAGE) and Western blot analyses were performed according to the manufacturers' instructions under non-reduced conditions.

Study Oversight

The preliminary dose-finding study was done in Sweden. Both transplantation studies had a phase I/II single-group design. The U.S. study was approved by the IRB at Cedars-Sinai Medical Center (IRB #37068). The Swedish study was approved by Uppsala regional ethics committee and the Swedish Medical Product Agency. The studies were conducted in accordance with the Declaration of Helsinki, with the ethical guideline based on federal regulations and the Common Rule. Cedars-Sinai Medical Center also has a federal-wide assurance. The data were gathered and analyzed and manuscript was prepared by the investigators.

Statistical Analysis

Statistical analysis of the characteristics of the patients and donors was performed with the use of a Mann-Whitney U test. The total serum IgG levels were compared with the use of a repeated-measures one-way analysis of variance with Dunn's multiple-comparison test. The highest levels of donor-specific antibodies were compared between the studies with the use of a repeated-measures one-way analysis of variance and Sidak's test for multiple comparisons. A P value of less than 0.05 was considered to indicate statistical significance.

Patient Characteristics

Figure 3:
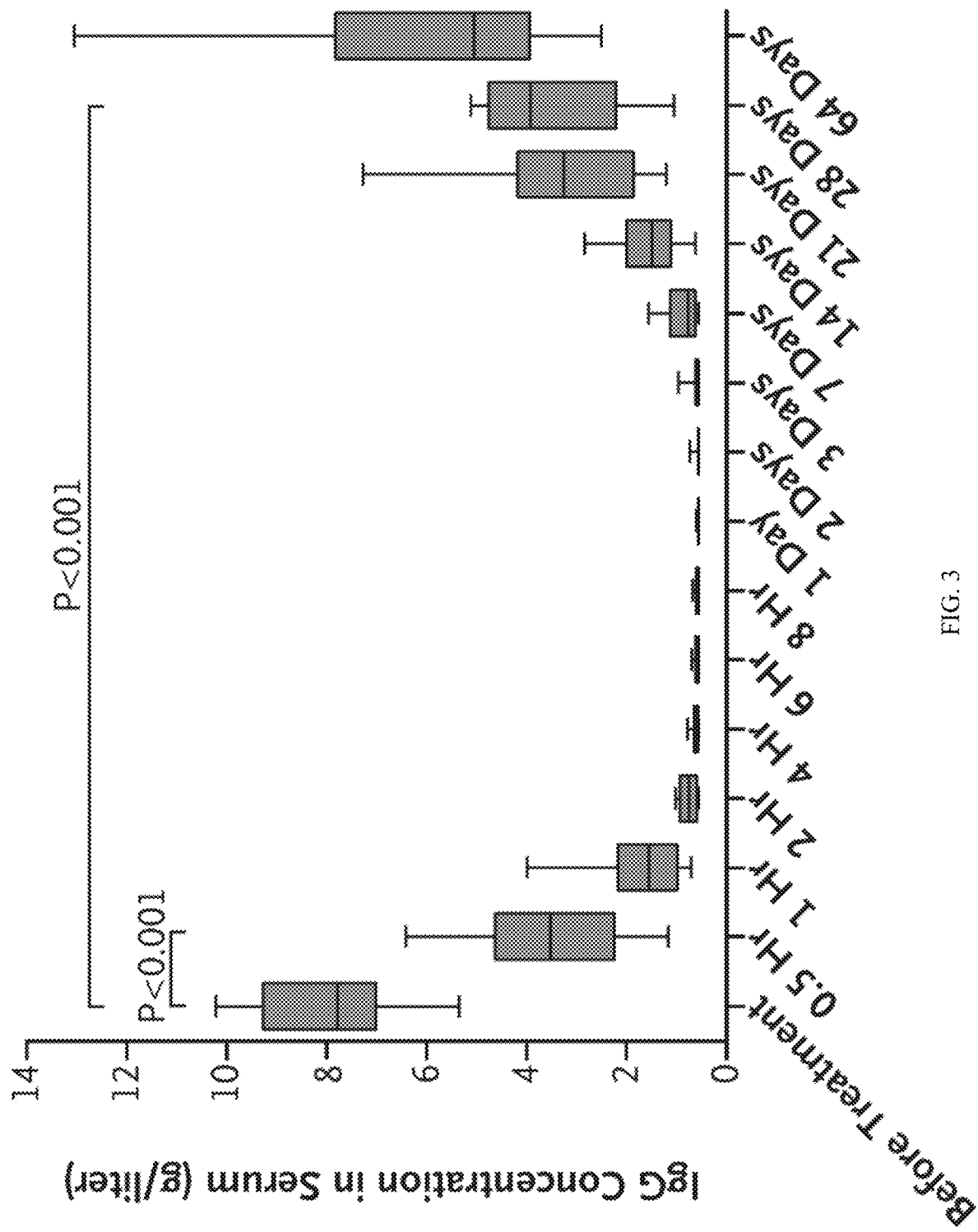
FIG. 3 is a box plot of total serum IgG collected before and at consecutive time-points following IdeS treatment (n=10 patients). The horizontal line in the boxes shows the median, the top and bottom of the boxes the interquartile range, and the I bars the range. P values were calculated by a repeated-measures oneway analysis of variance with Dunn's multiple-comparison test.
Figure 8:
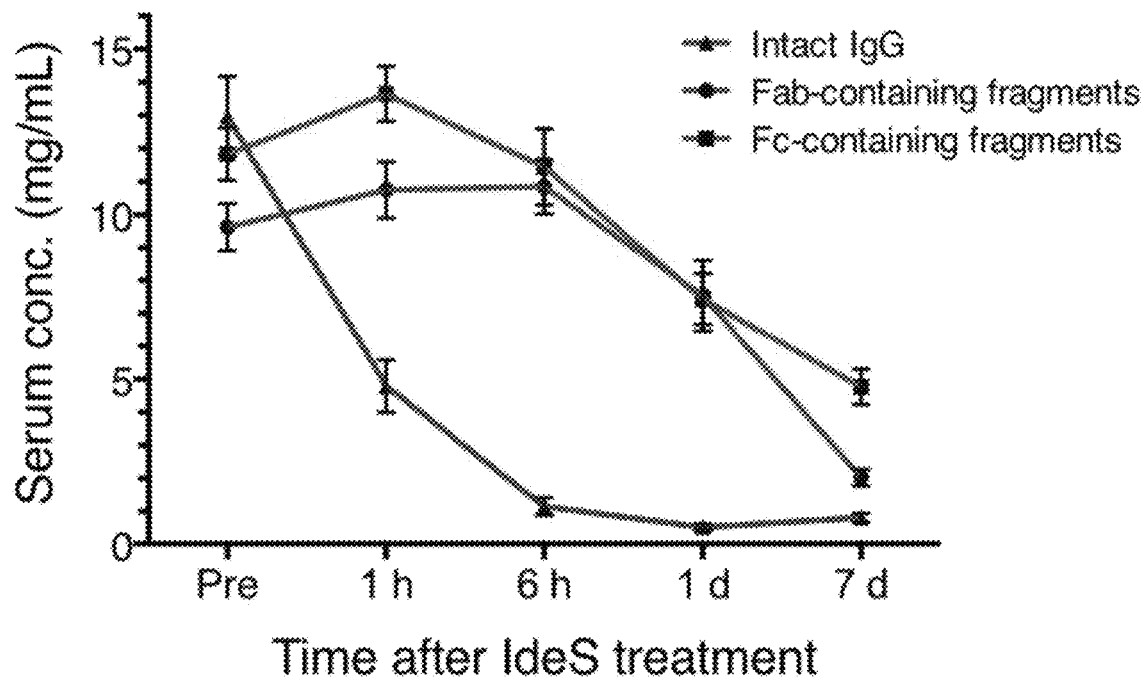
FIG. 8 shows, in accordance with various embodiments of the invention, the mean total IgG, F(ab')$_2$ and Fc fragments measured with ELISA pre- and post-IdeS treatment.

Eight patients with end-stage renal disease participated in the dose-finding study. An additional twenty-five highly sensitized patients who were undergoing dialysis and awaiting transplantation of a kidney from a deceased donor (DD) or a living donor (LD) were enrolled in the two transplant studies. The median calculated panel-reactive antibody level was 96% (range 82-100%) in the patients in the U.S. study and 81% (range 22-100%) in the patients in the Swedish study. Patients in the U.S. cohort had a significantly longer cold ischemia time (the time elapsed between procurement of the organ and transplantation), a significantly higher rate of delayed graft function, and a significantly higher mean fluorescence intensity for HLA class I antibodies at the time of transplantation than did those in the Swedish study. A total of twenty-two of the 25 patients had donor-specific antibodies present at the time of transplantation. No patient had detectable HLA antibodies or donor-specific antibodies immediately after transplantation. The characteristics of the patients and donors and the immunologic characteristics of the patients are shown in Table 1.

patible donor. Laboratory values were obtained prior to transplantation and at specified times after transplantation. A total of twenty-four of twenty-five patients had perfusion of allografts after transplantation. Subsequent assessments of SDS-PAGE, total IgG and Western blot analyses of patients' serum specimens obtained before and after treatment with IdeS were performed. SDS-PAGE analysis of serum specimens revealed reductions in total IgG beginning after IdeS infusion (FIGS. 2A-2D). By 6 hours after the start of the infusion, all the IgG molecules were completely cleaved into Fc and $F(ab')_2$ fragments, likely reducing their pathogenicity. All the IgG molecules are inactivated for approximately one to two weeks, when new IgG synthesis is detected. The large bands shown in the IgG region at 21 to 30 days occurred after the receipt of IVIg infusions. Western blot analysis confirmed the complete cleavage of IgG molecules into Fc and $F(ab')_2$ fragments. FIG. 8 shows the dynamics of total IgG, Fc and $F(ab')_2$ fragments in the serum specimens obtained from 10 IdeS-treated patients (n=10) as measured with ELISA techniques. Intact IgG levels begin to decline rapidly; little intact IgG was present at 6 hours after treatment with IdeS. No intact IgG was seen at or after 7 days. FIG. 3 shows serum IgG levels after treatment with IdeS in 10 patients in the Swedish study. There was a significant reduction in the total IgG level that persisted for 28 days.

TABLE 1

Characteristics of the Patients and Donors

|  | N | All | N | Sweden | N | US | P* |
|---|---|---|---|---|---|---|---|
| Recipient characteristics |  |  |  |  |  |  |  |
| Age (years), mean (SD) | 25 | 46.2 ± 14 | 11 | 52.4 ± 12.3 | 14 | 41.4 ± 13.9 | 0.05 |
| Gender male, no. (%) | 25 | 11 (44%) | 11 | 4 (36%) | 14 | 7 (50%) | 0.69 |
| At least 1 previous kidney transplant received, no. (%) | 25 | 14 (56%) | 11 | 5 (45%) | 14 | 9 (64%) | 0.27 |
| Donor characteristics |  |  |  |  |  | 13 (93%) |  |
| Deceased donor, no. (%) | 25 | 23 (92%) | 11 | 9 (82%) | 14 |  | 0.18 |
| Cold Ischemia Time (SD), hr | 25 | 15.8 ± 7.5 | 11 | 10.6 ± 6.8 | 14 | 19.9 ± 5.2 | <0.001 |
| Delayed graft function, no./total no. (%) | 24 | 10 (42%) | 11 | 0 (0%) | 13 | 10 (77%) | <0.001 |
| Immunologic variables |  |  |  |  |  |  |  |
| Anti-HLA DSA positive, no. (%) | 25 | 23 (92%) | 11 | 9 (82%) | 14 | 14 (100%) | 0.18 |
| No. of anti-HLA DSA, mean (SD) | 23 | 2.3 ± 1.8 | 9 | 2.2 ± 1.6 | 14 | 2.4 ± 1.9 | 0.79 |
| Mean fluorescence intensity of Class I, mean (SD) | 16 | 5659.6 ± 2364.1 | 6 | 4192.5 ± 2372 | 10 | 6375 ± 1996 | 0.04 |
| Mean fluorescence intensity of Class II, mean (SD) | 16 | 8198.9 ± 5639.2 | 6 | 10464 ± 7050.9 | 10 | 6500 ± 3570.7 | 0.06 |
| Negative Anti-HLA DSA at 1 to 6 hr after treatment, no. (%) | 25 | 25 (100%) | 11 | 11 (100%) | 14 | 14 (100%) | >0.99 |
| Positive Cross-match at transplantation, no. (%)** | 25 | 20 (80%) | 11 | 7 (64%) | 14 | 14 (100%) | 0.13 |
| Estimated GFR at 1 to 6 mo after transplantation, |  |  |  |  |  |  |  |
| ml/min/1.73 m² | 24 | 58 ± 30 | 11 | 49 ± 13 | 13 | 70 ± 36 | 0.14 |
| Follow-up, mo. | 24 | 4.7 ± 1.9 | 11 | 5.7 ± 0.9 | 13 | 4.0 ± 2.4 | 0.03 |
| Graft loss, no. (%) | 25 | 1 (4%) | 11 | 0 (0%) | 14 | 1 (7%) | >0.99 |

*Plus-minus values are means ±SD. Data on the number of anti-HLA donor-specific antibodies were missing for two patients in the Swedish study, data on the mean fluorescence intensity for five patients in the Swedish study and for four in the U.S. study, and data on the estimated glomerular filtration rate (GFR) and duration of follow-up for one patient in the U.S. study. Statistical analysis was performed with the use of a Mann-Whitney U test. A P value of less than 0.05 was considered to indicate statistical significance.
**Positive cross-match was defined as a T-cell flow-cytometric result that was greater than 50 mean channel shifts, a T-cell pronase result that was greater than 70 mean channel shifts, a B-cell flow-cytometric result that was greater than 100 mean channel shifts, and a B-cell pronase result that was greater than 130 mean channel shifts. Cross-match positivity was not a requirement for inclusion in the Swedish trial, whereas the U.S. trial required donor-specific antibody positivity or cross-match positivity (or both).

IdeS and Serum IgG Levels

Figure 4A:
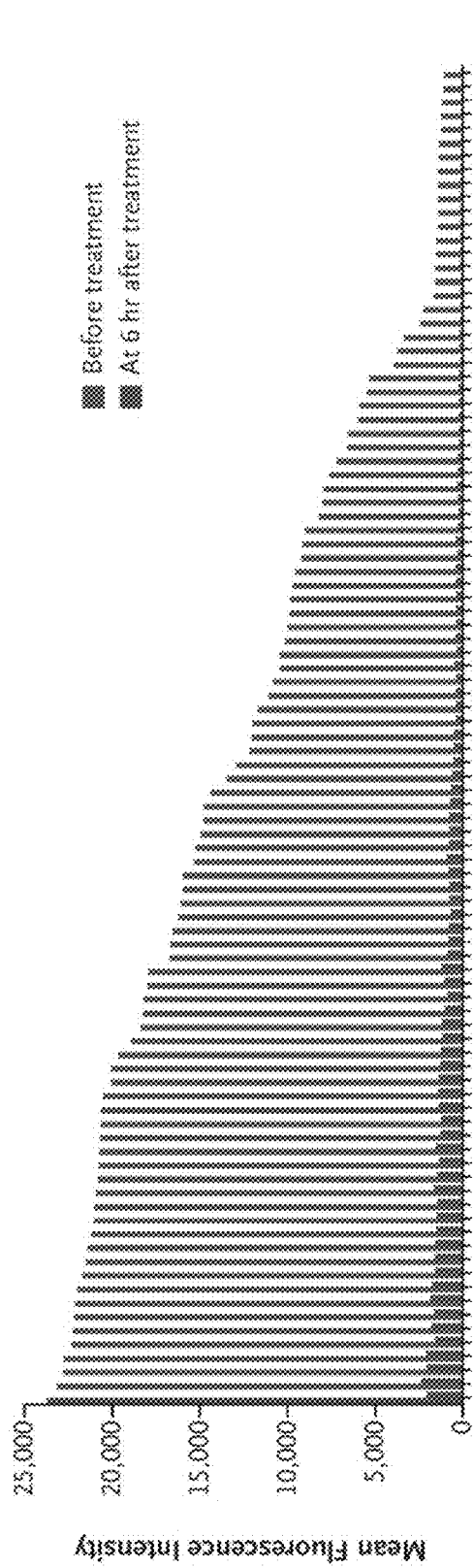
FIGS. 4A and 4B depict the levels of HLA-antibodies binding to 97 different HLA antigens (4A) and C1q Binding HLA-antibodies (4B) following IdeS administration, respectively. Each tick mark on the x axis indicates a single HLA antigen. IdeS was used to reduce pathogenic HLA antibodies and C1q binding HLA antibodies as part of a dose-finding study involving 8 patients with end-stage renal disease (ESRD) in Uppsala, Sweden (NCT: 02224820).
Figure 4B:
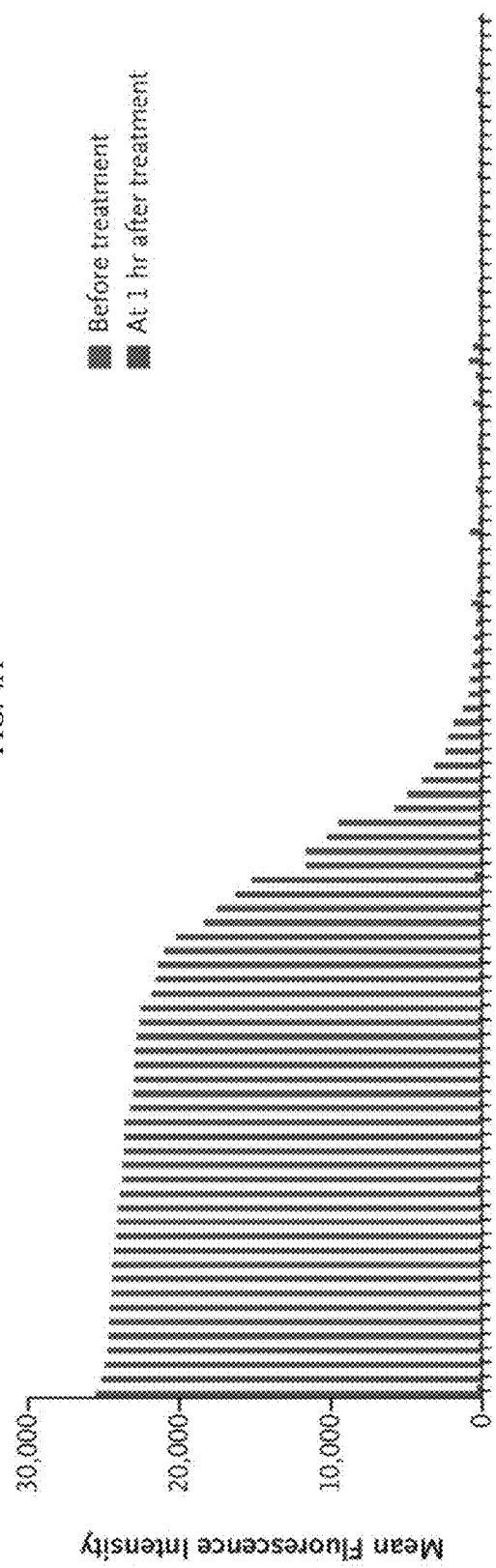

Patients were admitted to hospital prior to transplantation and received IdeS over 15 minutes approximately four to 6 hours prior to receiving a kidney transplant from an incom- HLA Antibody and Donor Specific Antibody Levels Complement-activating donor-specific antibodies are known to severely injure and rapidly destroy the allograft. Thus, IdeS would need to inactivate pathogenic donor-specific antibodies, specifically those that can activate complement, if it will work as a potential desensitization agent. The dose-finding study involving 8 HLA-sensitized patients who were undergoing dialysis (Sweden) evaluated the ability of IdeS to reduce the levels of C1q-binding and total HLA antibodies. Data from a representative patient with multiple, strong C1q-binding HLA antibodies is shown in FIG. 4A and FIG. 4B. Briefly, near-complete inhibition of C1q-binding HLA antibodies was seen one hour after treatment. The levels of all HLA antibodies were significantly reduced at 6 hours after treatment.

Figure 9:
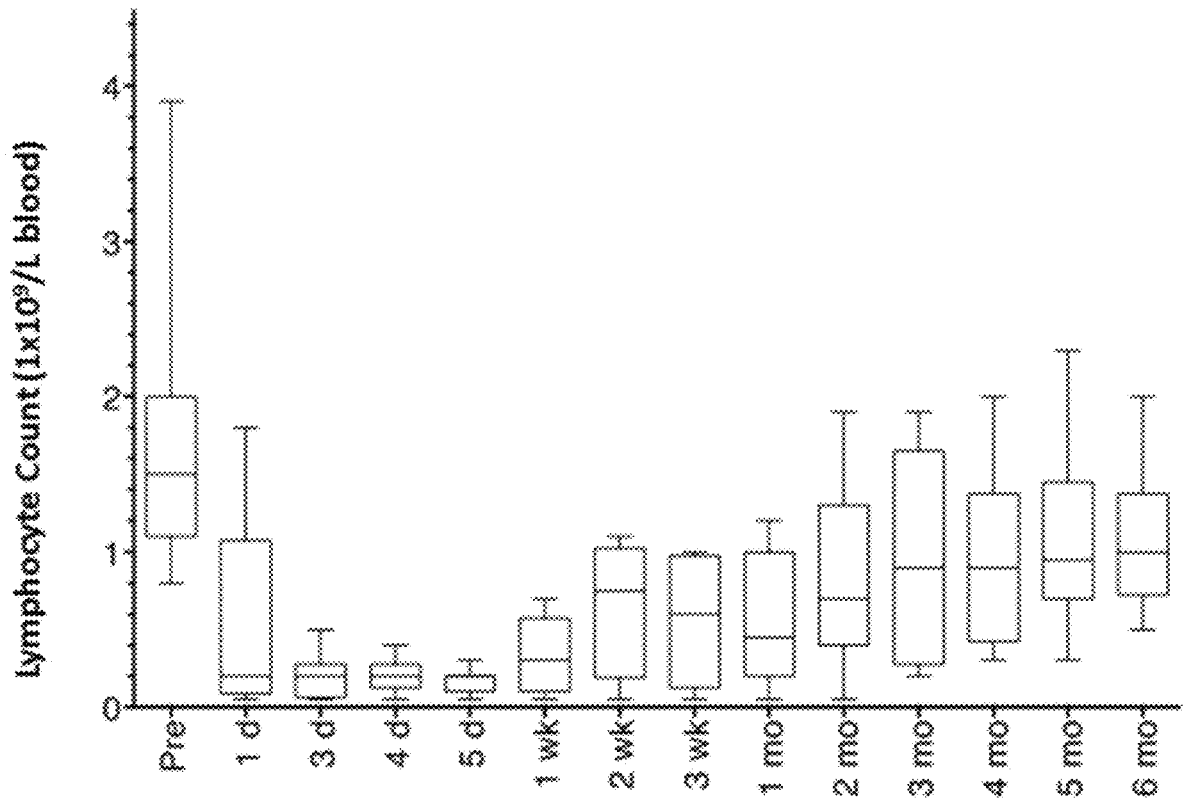
FIG. 9 shows, in accordance with various embodiments of the invention, a box plot of total lymphocyte count in blood samples collected before and at consecutive time-points following IdeS treatment from patients treated with eATG for induction.
Figure 10A:
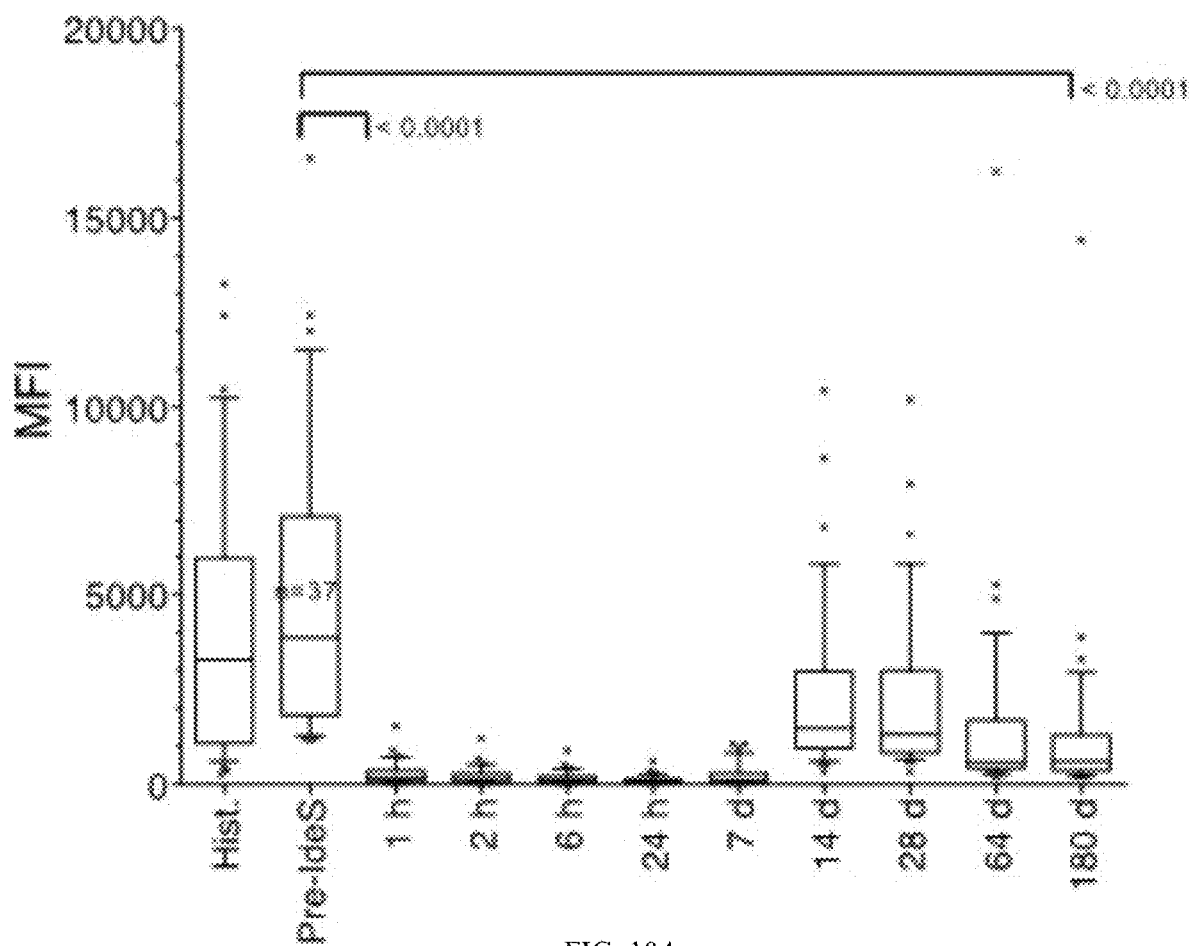
FIGS. 10A-10F show human leukocyte antigen antibodies and non-donor antibodies dynamics after IdeS treatment and transplantation in Swedish patients.
Figure 10B:
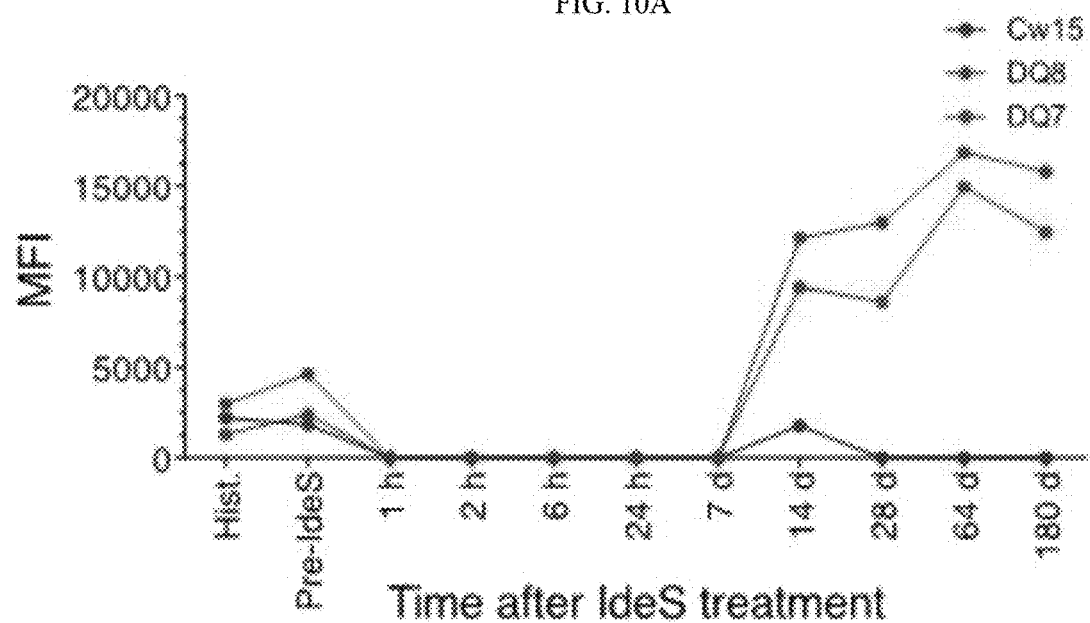
Figure 10C:
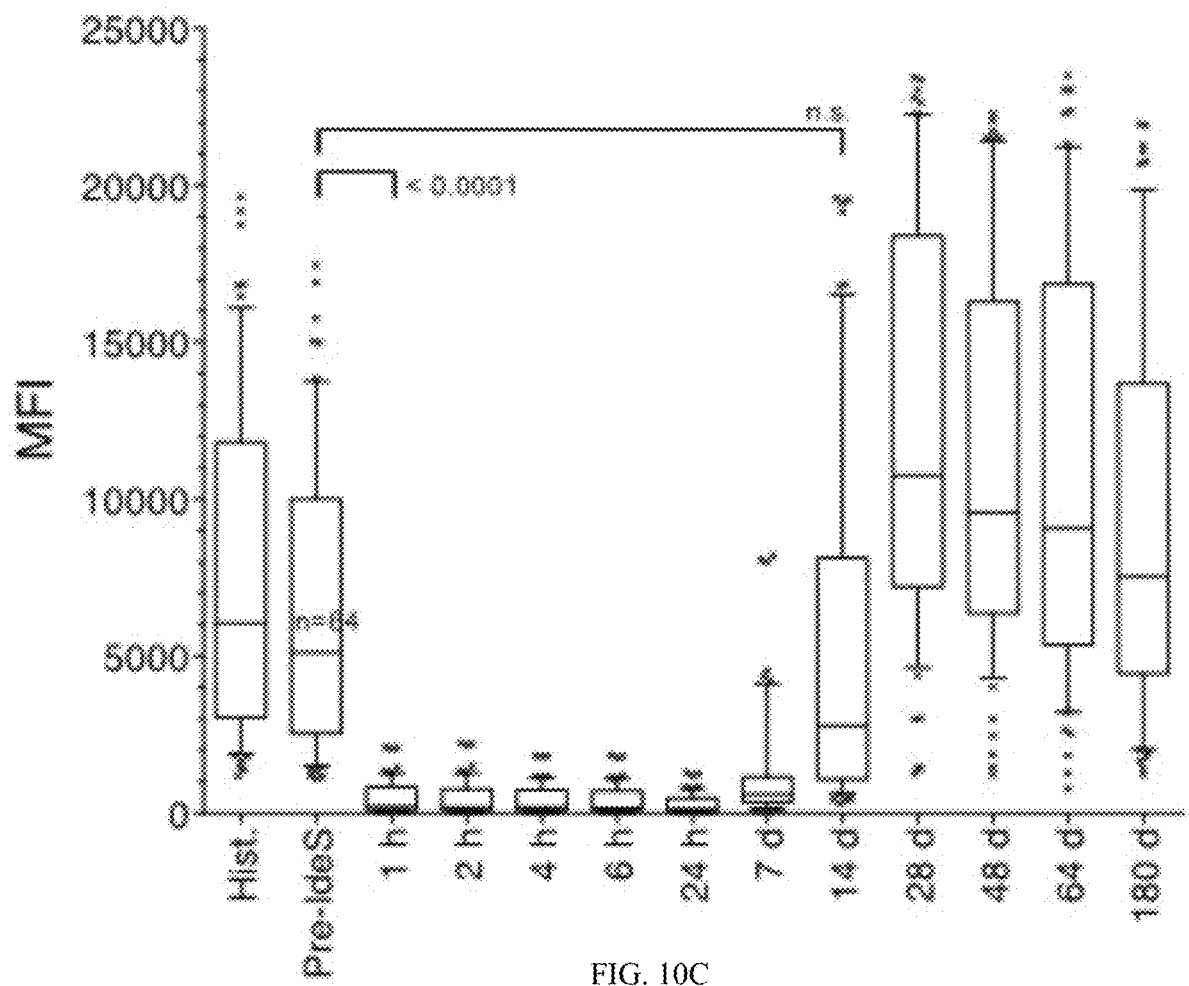
Figure 10D:
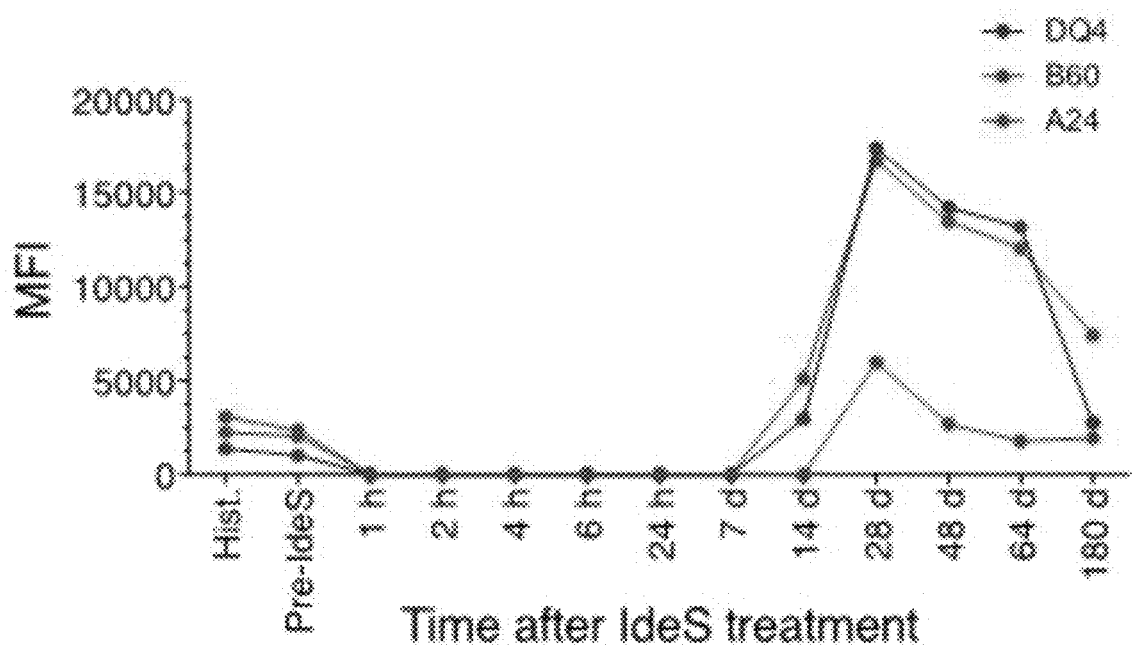
Figure 10E:
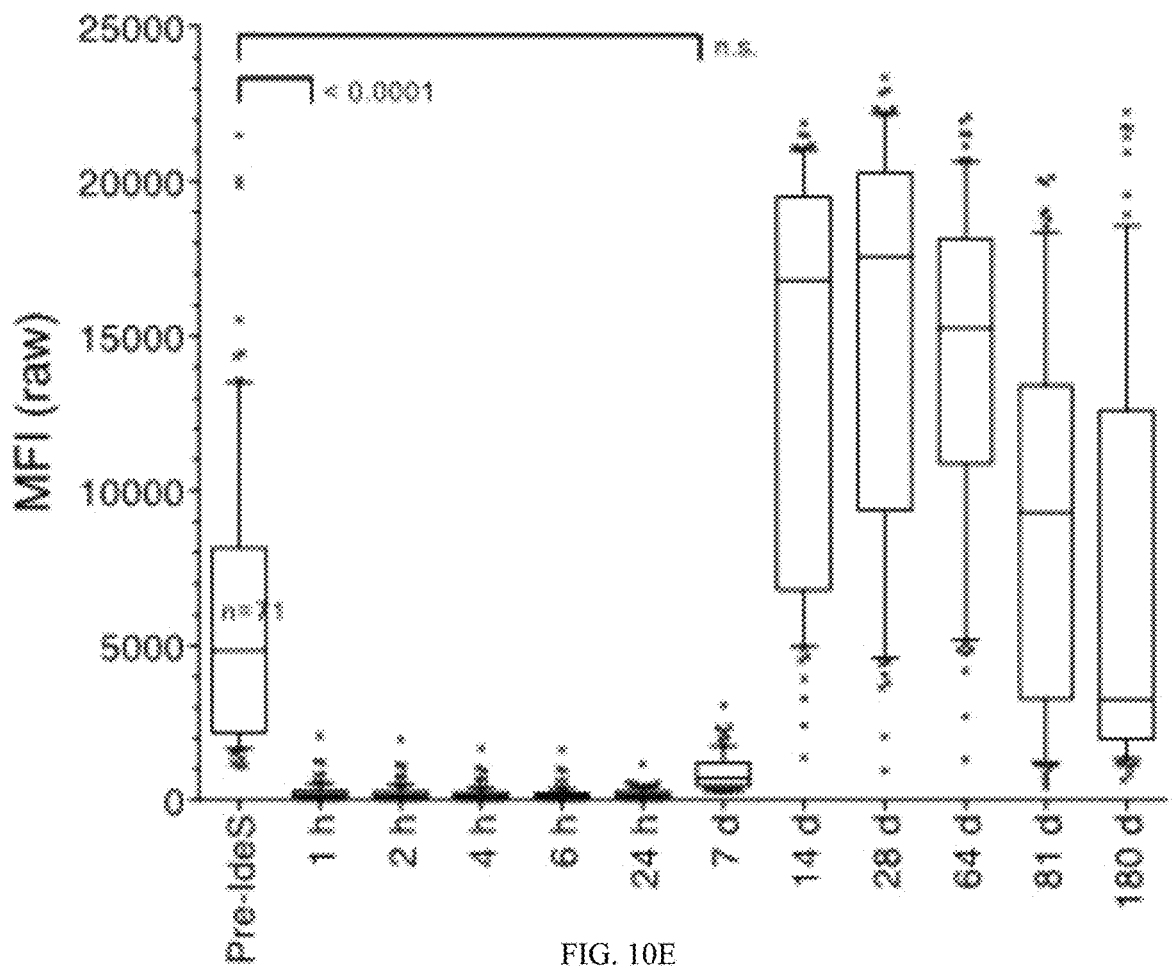
Figure 10F:
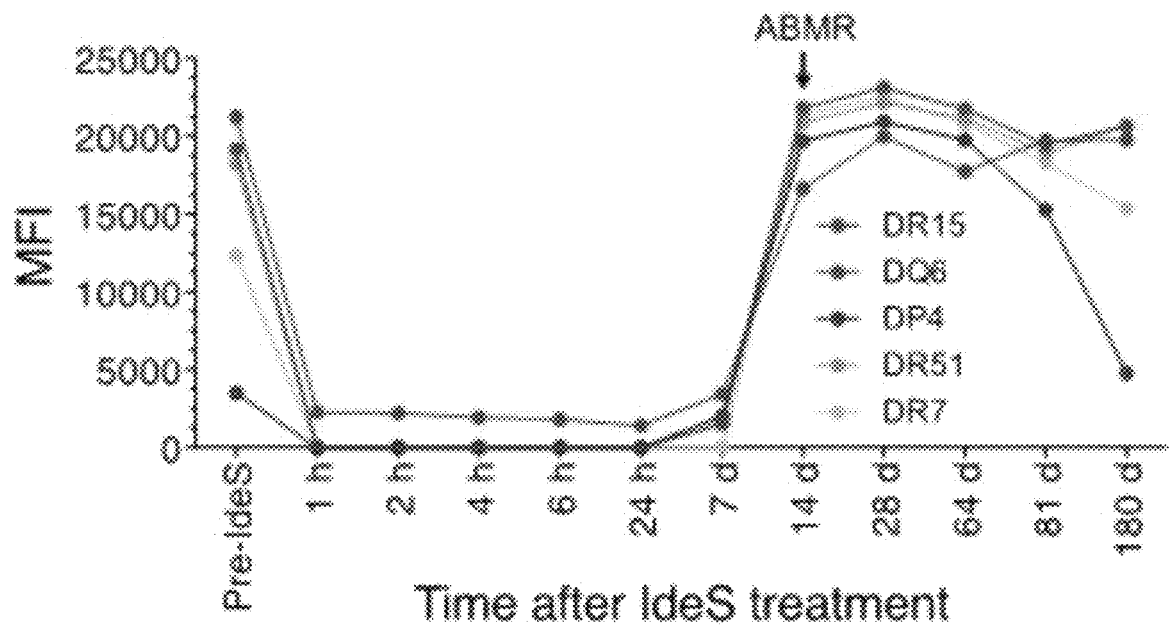
Figure 11A:
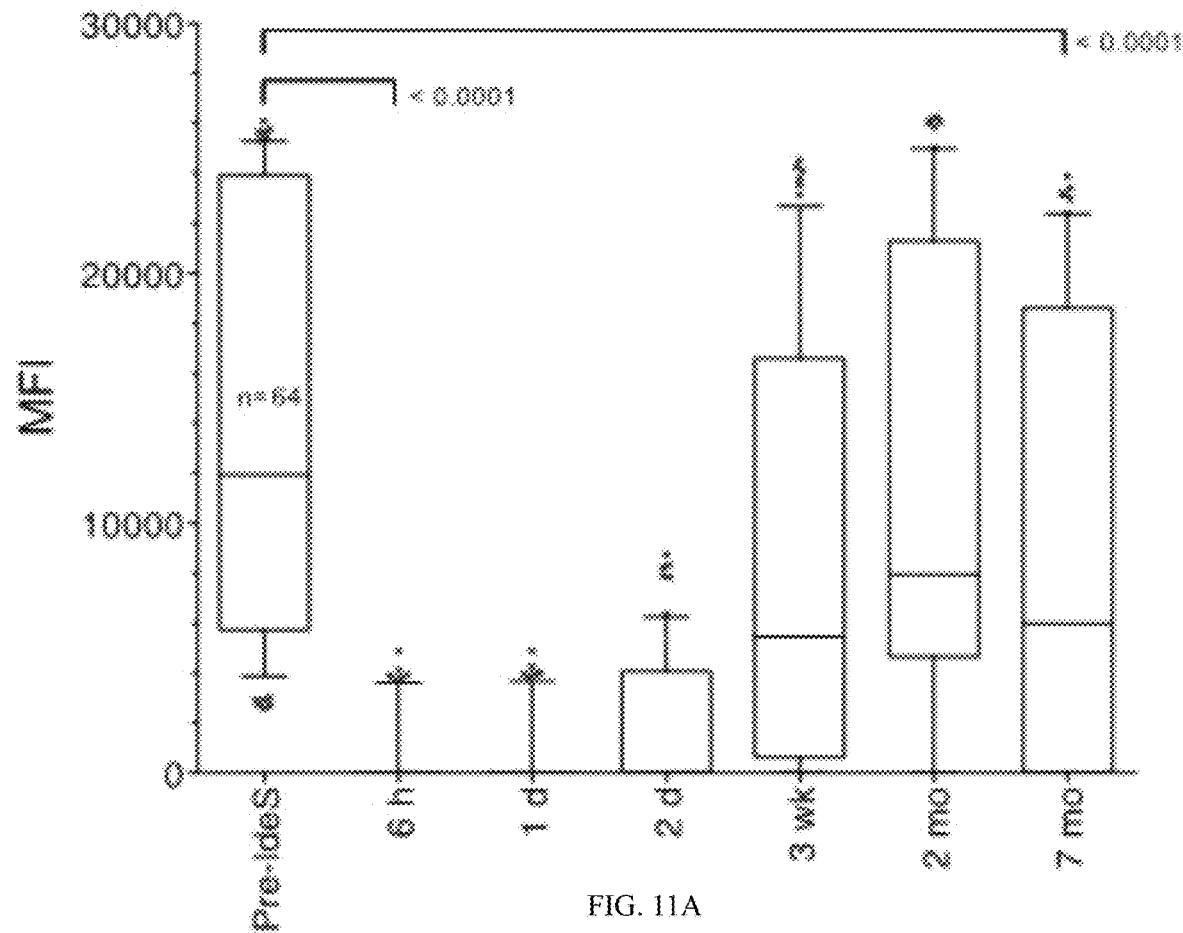
FIGS. 11A-11F show human leukocyte antigen antibodies and non-donor antibodies dynamics after IdeS treatment and transplantation in US patients.
Figure 11B:
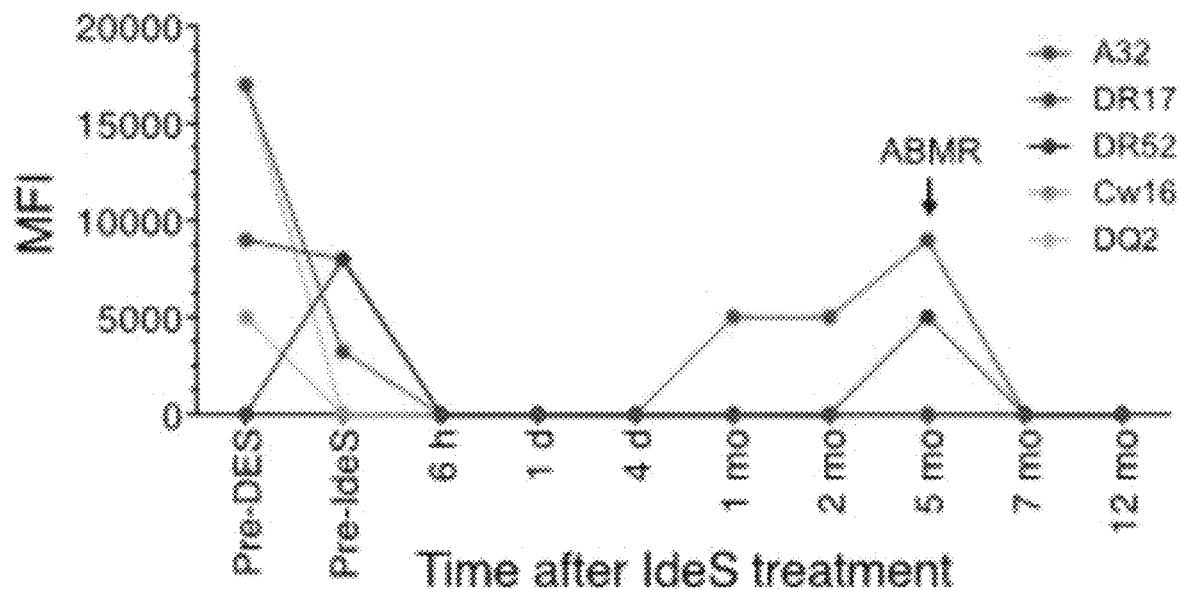
Figure 11C:
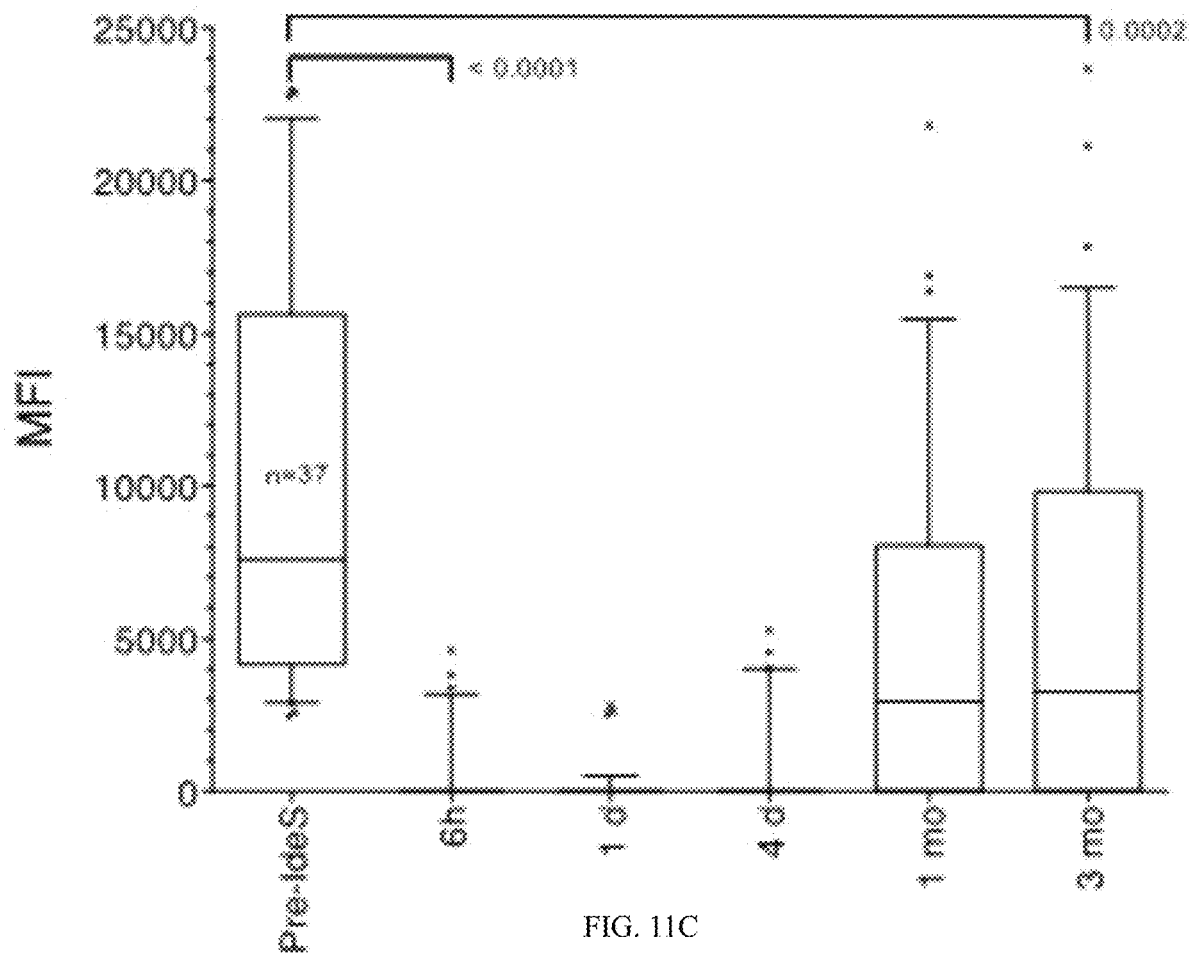
Figure 11D:
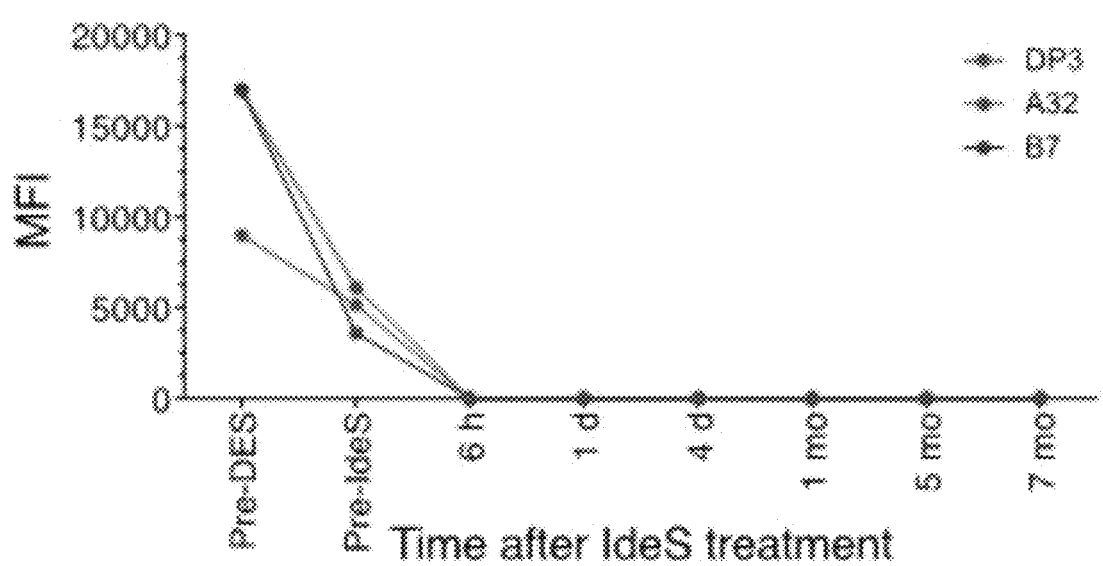
Figure 11E:
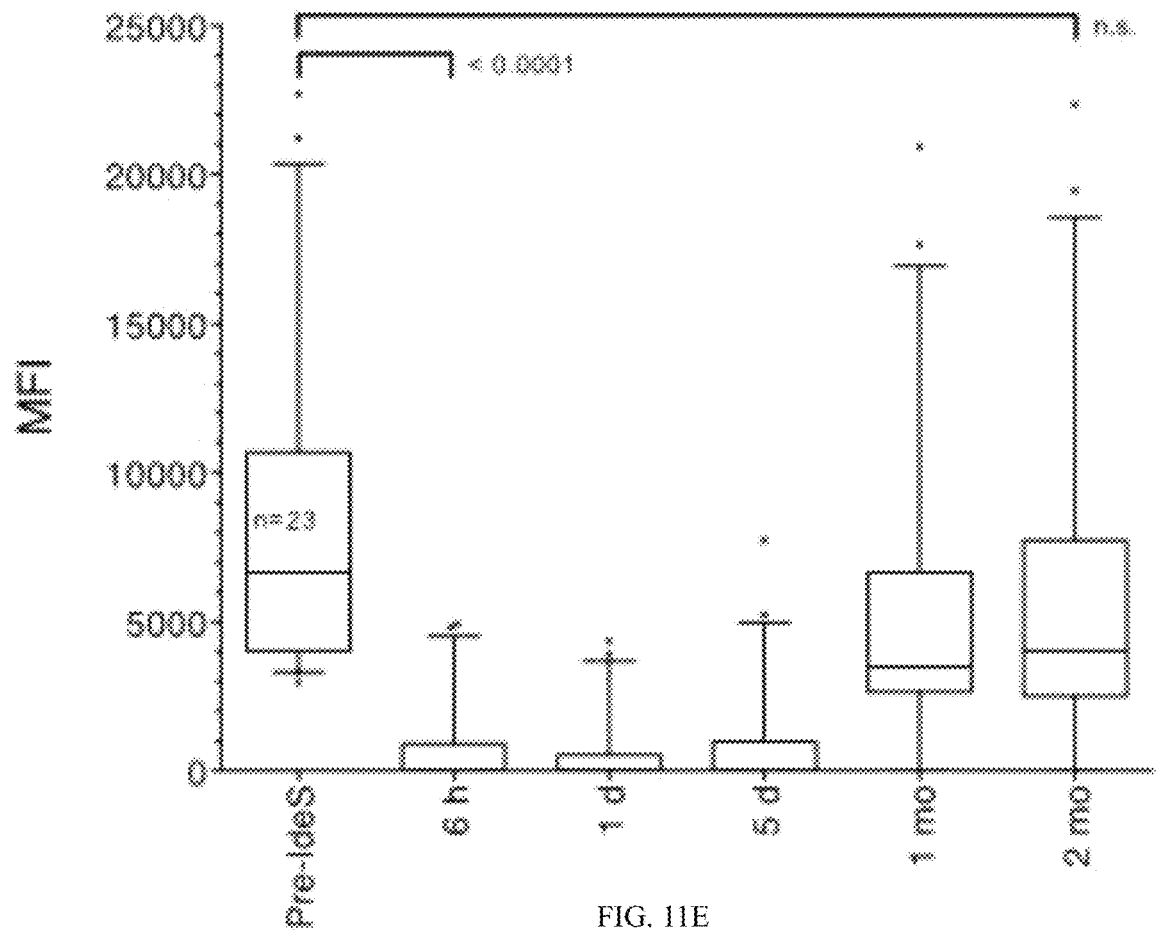
Figure 11F:
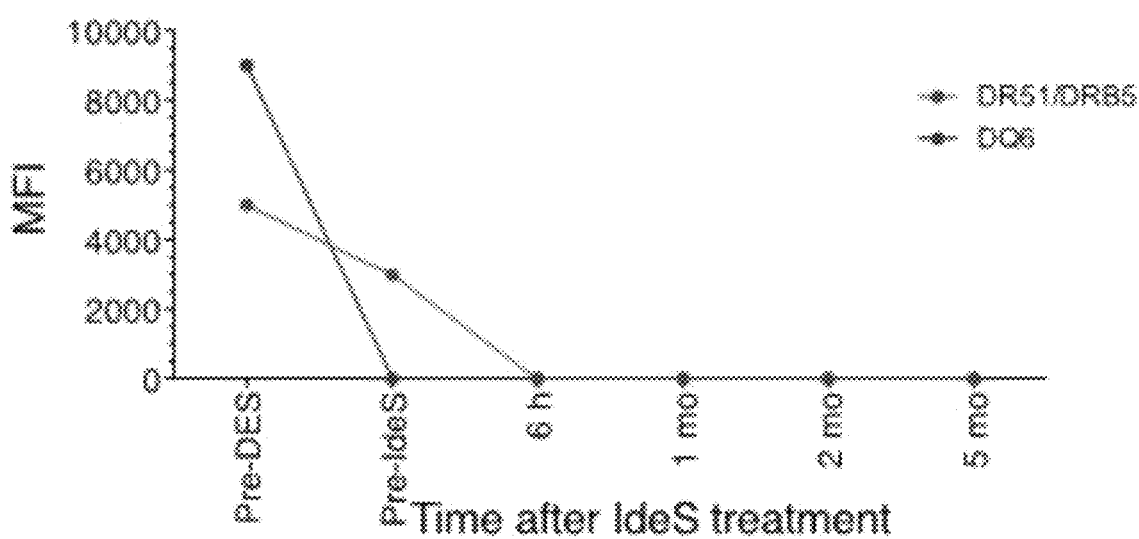

We also examined sequential lymphocyte counts before and after treatment with IdeS in 8 patients in the Swedish study who underwent transplantation and received induction with horse antithymocyte globulin (FIG. 9). The course of lymphocyte depletion and repletion was similar to that observed in previously reported 36 patients in the U.S. who underwent transplantation after desensitization without IdeS.

Figure 5A:
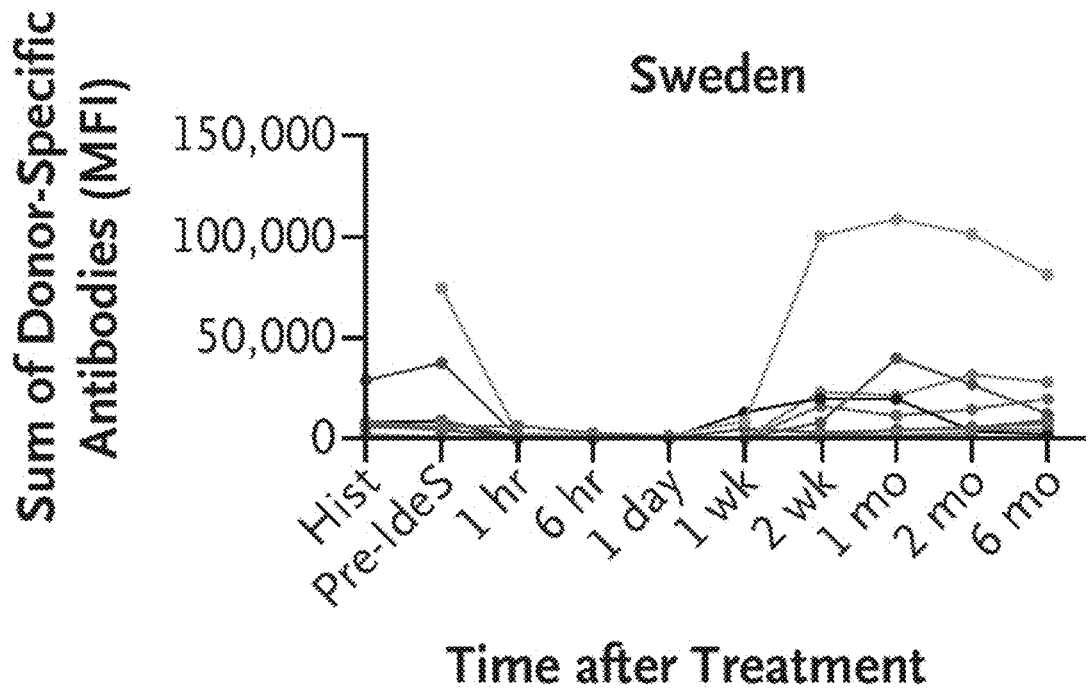
FIGS. 5A-5D show the comparison of the sum of all donor-specific antibodies (5A, 5C) and the highest levels of donor-specific antibodies (5B, 5D) for 9 patients treated in the Swedish study (5A, 5B) and among 14 patients treated in the US study (5C, 5D). Levels were assessed according to the mean fluorescence intensity (MFI). Hist denotes historical data, and DES desensitization.
Figure 5B:
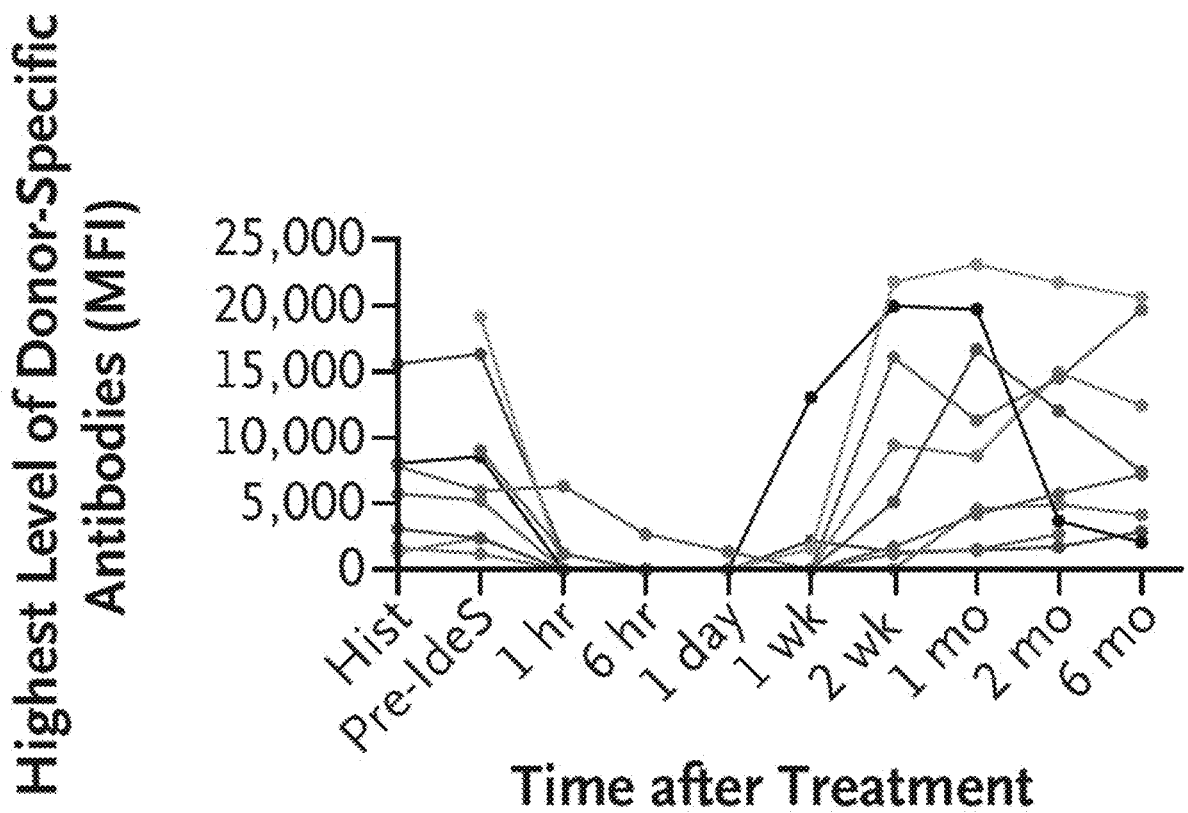
Figure 5C:
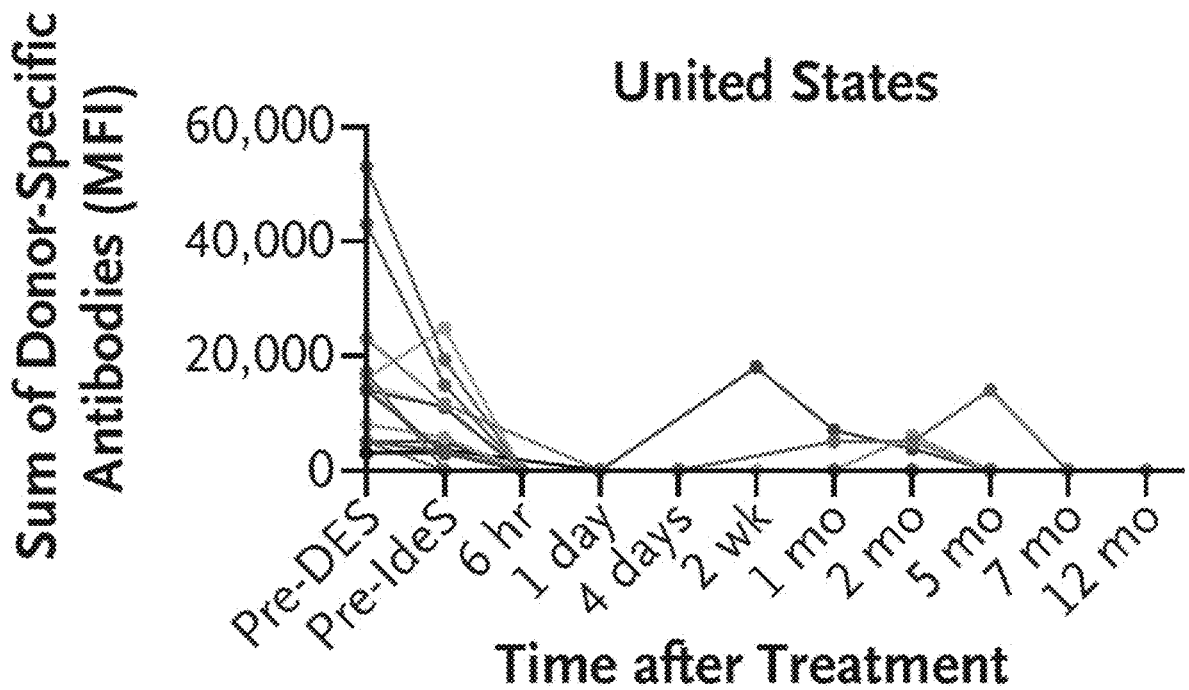
Figure 5D:
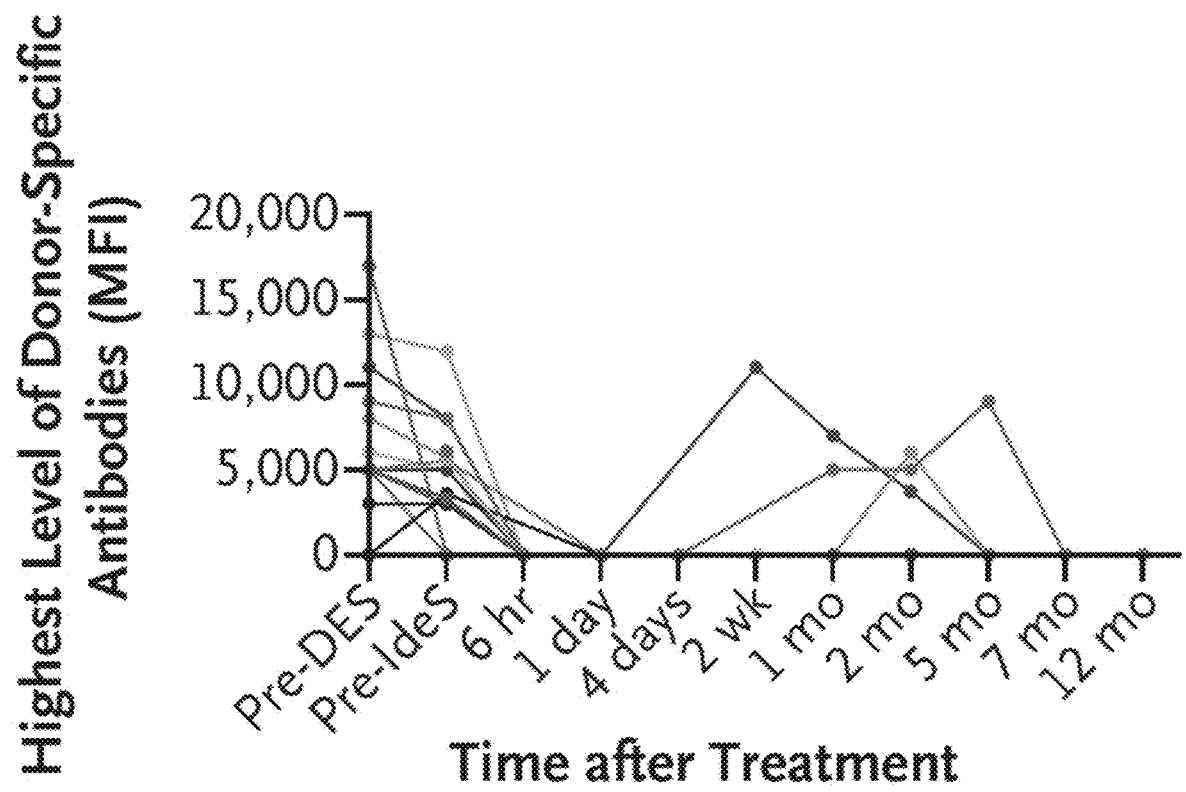
Figure 5E:
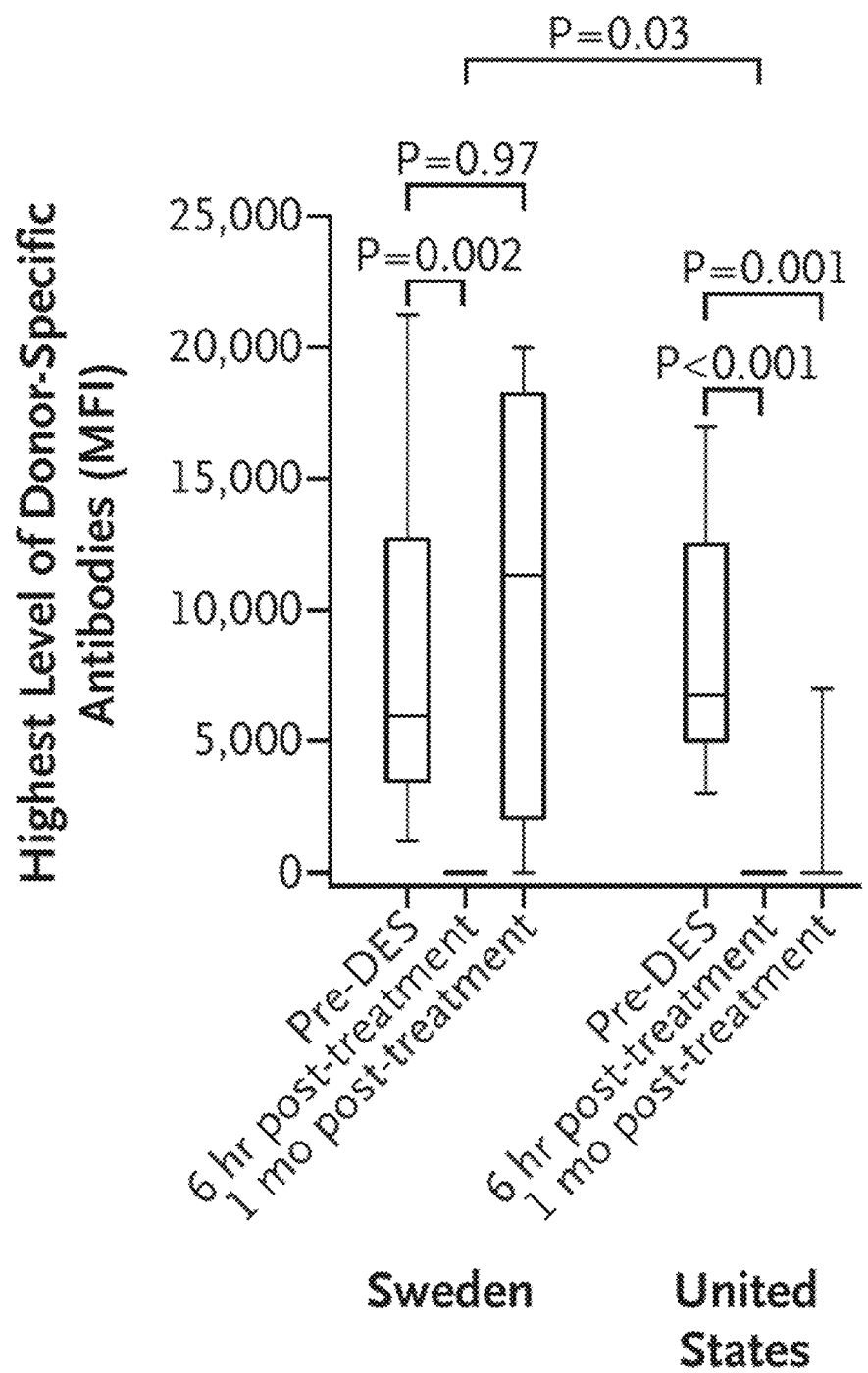
FIG. 5E shows a comparison of the median highest levels of donor-specific antibodies before desensitization and at 6 hours and 1 month after IdeS treatment; the horizontal line in the boxes shows the median, the top and bottom of the boxes the interquartile range, and the I bars the range. The data show a significant difference in donor-specific—antibody rebound between the studies; results are from a repeated-measures one-way analysis of variance and Sidak's test for multiple comparisons.

We assessed the level of circulating HLA antibodies and donor-specific antibodies at multiple time points before treatment with IdeS and after transplantation. All the patients had near-complete or complete reductions of levels of HLA antibodies and donor-specific antibodies at 6 hours and 24 hours after treatment. Data are presented separately for the Swedish and U.S. cohorts. The mean donor-specific antibody levels for both groups before treatment and at 6 hours and one month after treatment are shown in FIGS. 5A-5E. Despite similar levels of donor-specific antibodies prior to transplantation in the U.S. and Swedish studies, significant reduction in the sum of donor-specific antibodies and reduction in the highest levels of donor-specific antibodies were seen in the U.S. cohort at 1 month after transplantation (FIG. 5E). FIGS. 10A-10F show representative data from three patients in the Swedish study. Levels of HLA antibodies and donor-specific antibodies remained undetectable until 7 to 14 days after transplantation, when rebound occurred. In contrast, the U.S. cohort had fewer patients with rebound and lower levels of HLA antibodies after desensitization treatment with IdeS (FIGS. 11A-11F). Thus, in all, significant differences were seen between the groups of patients in the U.S. study and the Swedish study, indicating that the anamnestic responses were blunted in the patients in the U.S. study at one month, which was believed to reflect the use of IVIg plus rituximab before and after transplantation.

Clinical Outcomes

Figure 6A:
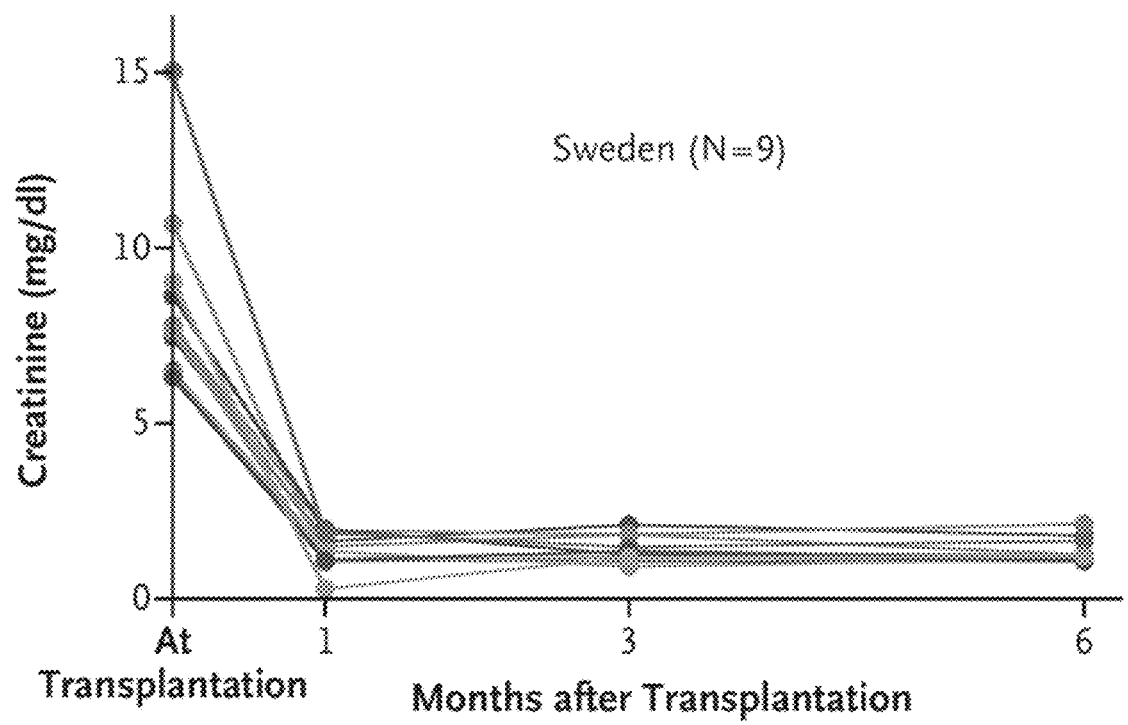
FIGS. 6A and 6B show the course of serum creatinine levels before and after transplantation in patients in the two studies. Overall the renal function was good, although 1 patient in the U.S. study had prolonged delayed graft function that was due to suboptimal quality of the donated kidney. To convert creatinine values to micromoles per liter, multiply by 88.4.
Figure 6B:
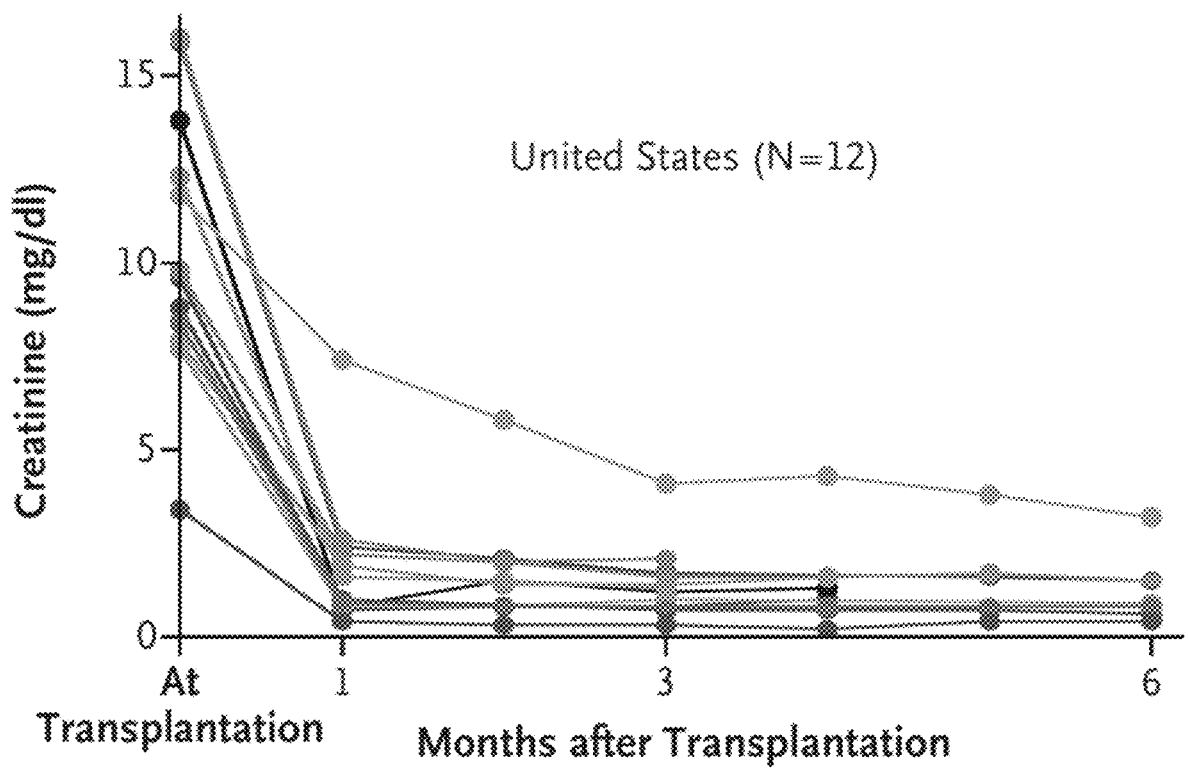
Figure 7A:
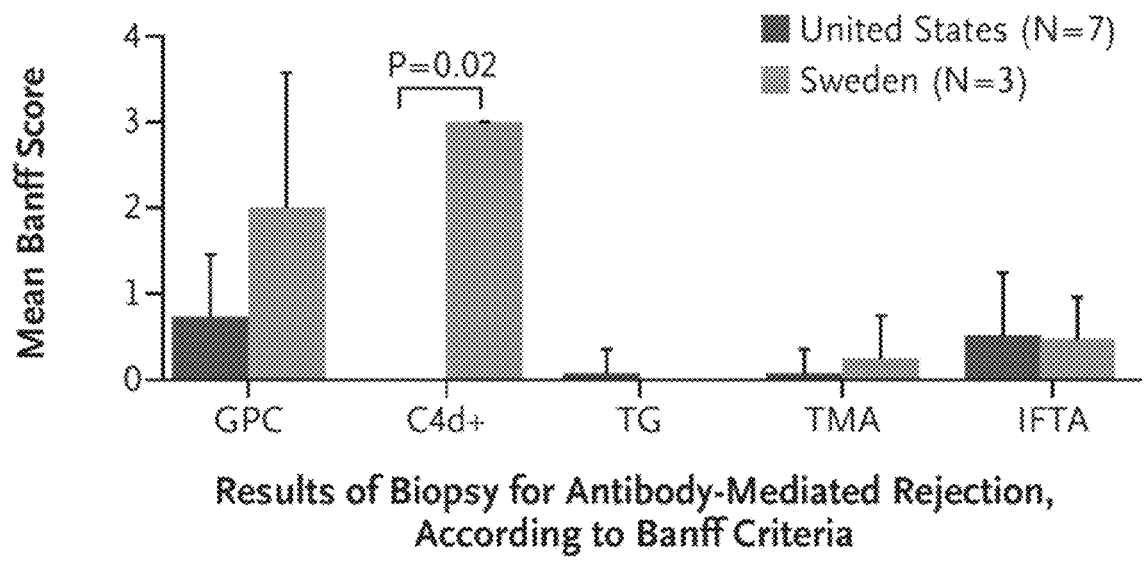
FIGS. 7A and 7B show the pathological features of biopsies performed because of antibody-mediated rejection in 7 patients in the U.S. study and in 3 in the Swedish study in whom antibody-mediated rejection developed after transplantation (7A); and the pathological features of per-protocol biopsies performed at 6 months after receipt of IdeS in 7 patients in the U.S. study and in 9 patients in the Swedish study (7B). Scoring of various values (complement factor 4d deposition [C4d+], interstitial fibrosis and tubular atrophy [IFTA], glomerulitis plus peritubular capillaritis [GPC], transplant glomerulopathy [TG], and thrombotic microangiopathy [TMA]) was based on Banff 2013 criteria. T bars indicate 1 SD. Significantly less C4d deposition was seen in the U.S. cohort than in the Swedish cohort.
Figure 7B:
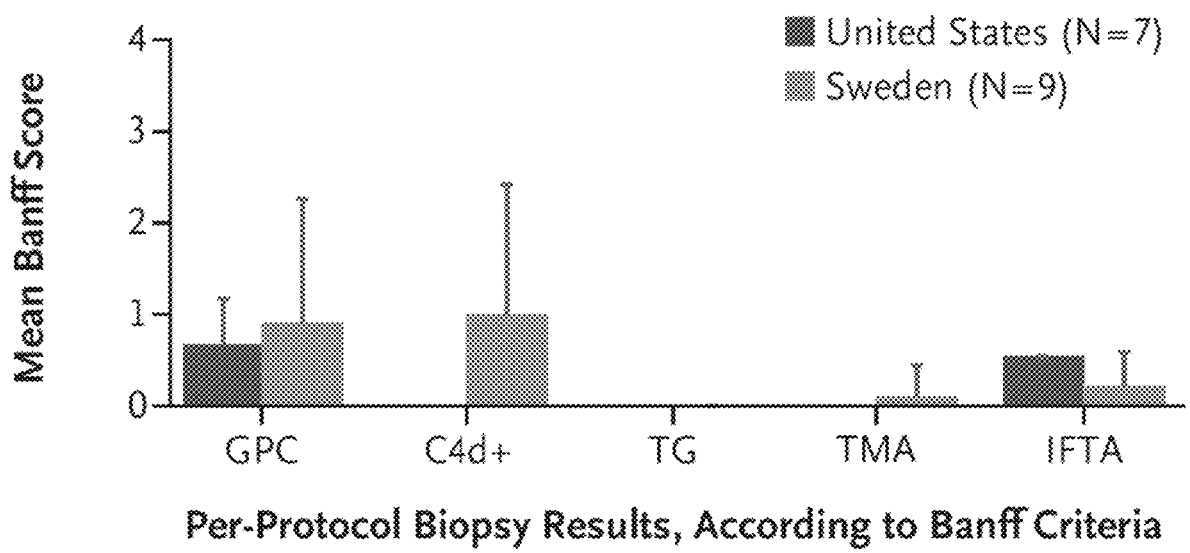

Three patients in the Swedish group experienced antibody-mediated rejection at a mean two weeks post-transplantation that was associated with rebound of donor specific antibodies and C4d+ on biopsies. Per-protocol biopsies that were performed at 6 months showed minimal inflammation in 9 of 11 patients. Seven patients in the U.S. study had inflammation on renal biopsy that was detected at a mean of 3.6 months post-transplantation. Two patients in the U.S. study met the strict Banff 2013 criteria for antibody-mediated rejection (detected at 5 months and at two months after IdeS treatment); the rejection was associated with a rise in the levels of donor-specific antibodies and resolved after treatment. Renal function was generally good for both groups post-transplantation (FIGS. 6A and 6B). The pathologic features on biopsy specimens obtained from patients with antibody-mediated rejection and on the specimens obtained in per-protocol biopsies conducted at 6 months in the two studies are shown in FIGS. 7A and 7B. Here, the patients with antibody rejection in the Swedish study had higher C4d+ scores than did those in the U.S. study, (FIG. 7A), whereas low levels of inflammation were seen in the per-protocol biopsies that were conducted in the two groups at 6 months post-transplantation (FIG. 7B). One patient in the U.S. study experienced hyperacute rejection immediately after re-vascularization. This event was unexpected, since the tests for cross-matches and donor-specific antibodies were negative after IdeS treatment and before transplantation. Extensive investigations after the rejection showed high-titer IgM and IgA antibody reactive with donor-allograft endothelium, which we speculate was likely responsible for the immediate graft loss. Subsequent assessments showed no evidence of IgM anti-HLA or donor-specific antibodies. Thus, the antibody appears to be a non-HLA antibody that cannot be cleaved by IdeS.

Adverse Events

The possibility of serious infectious complications related to IdeS treatment was an anticipated concern. Previous data from healthy volunteers in a phase 1 study showed no signal for increased infection after IdeS infusion. In the U.S cohort, we observed no significant infectious complications. Patients were monitored monthly for cytomegalovirus (CMV), Epstein-Barr virus (EBV), polyoma-virus type BK, and JC viremia. with no patients having positivity.

A complete summary of serious adverse events (SAEs) is shown in Table 2. No deaths occurred in this study. A total of 38 SAEs were observed in 15 patients; five of these events were considered by the investigators as being possibly attributable to IdeS. There were 13 infectious complications that generally responded to treatment. However, in the Swedish study, one patient had prolonged parvovirus B19 viremia and one had persistent myalgias after the IdeS infusion.

Table 2: Serious Adverse Events (SAEs) and their Association with IdeS

TABLE 2

Serious Adverse Events (SAEs) and their association with IdeS

| SAE | No. of events | Investigators' Assessment of Relatedness of Event to Ides treatment* |
|---|---|---|
| Bacterial Infection | | |
| Urinary Tract | 5 | NR |
| Blood | 3 | PR (in 1), ULR (in 2) |
| Abdominal | 1 | PR |
| Catheter Side | 1 | PR |
| Pneumonia | 2 | ULR (in 1), NR (in 1) |
| Viral Infection with Parvovirus** | 1 | PR |
| Lymphocele | 1 | NR |
| Renal-artery Stenosis | 1 | NR |
| Ureteric Obstruction | 2 | NR |
| Cholelithiasis or Cholecystitis | 2 | ULR (in 1), NR (in 1) |
| Leukopenia | 1 | NR |
| Elevated creatinine level | 1 | NR |
| ABMR | 5 | NR |
| CMR | 1 | NR |
| Both ABMR and CMR | 2 | NR |
| ABMR mediated by IgM antibody | 1[a] | NR |
| Abdominal Pain | 3 | NR |
| Anemia | 1 | NR |

TABLE 2-continued

Serious Adverse Events (SAEs) and their association with IdeS

| SAE | No. of events | Investigators' Assessment of Relatedness of Event to Ides treatment* |
|---|---|---|
| Fever | 1 | NR |
| Cardiovascular (Afib) & CHF Exacerbation | 1 | NR |
| Malignant Hyperthermia | 1 | NR |
| Myalgia** | 1 | PR |

Abbreviations-NR, not related; PR, possibly related; ULR, unlikely related; SAE, significant adverse events; ABMR, antibody mediated rejection; CMR, cell mediated rejection; HyperIgM, hyper-immunoglobulin M; Afib, atrial fibrillation; CHF, congestive heart failure.
**All SAEs were resolved (patients recovered) except for the event of myalgia; which is an ongoing SAE.
$^a$Rejection was counted per patient rather than per event.

Outcomes for IdeS treated patients from both cohorts were good, including similar graft survival and overall survival among patients, renal function, and incident of antibody mediated rejection up to 1.5 years post-transplant. Administering IVIg and an anti-CD20 agent following transplantation resulted in significant reductions in the sum of donor-specific antibodies and reduction in the highest levels of donor-specific antibodies at 1 month after transplantation, as seen in the U.S. cohort compared to that in the Swedish cohort. Reducing or eliminating donor-specific antibodies, as realized following IdeS treatment, allowed for successful transplantation in 24 of 25 patients. The single allograft loss was due to hyperacute rejection in a patient who appeared to have a non-HLA antibody.

Nearly fifty years ago, Terasaki and Russell identified alloantibodies as major immunologic barriers to successful transplantation and graft survival. Despite advancements in desensitization, the efficient removal of pathogenic human leukocyte antigen (HLA) antibodies is still a considerable medical challenge.

In 2002, a cysteine protease was discovered and purified from *Streptococcus pyogenes* (IdeS). It has a unique specificity for IgG and is a potent virulence factor produced by *S. pyogenes*, because removing the Fc region of host IgG essentially ablates humoral immunity given that cleaved IgG can no longer activate complement or mediate antibody-dependent cellular cytotoxicity. Thus, inactivation of IgG-mediated effector pathways by IdeS should help prevent antibody-mediated cytotoxicity. Thus, the inactivation of IgG-mediated effector pathways by IdeS may help to prevent antibody-mediated injury to allografts. IdeS also cleaves B-cell receptors from circulating B cells, with the resultant inhibition of antigen-specific B-cell IgG responses in vitro. However, the risk of rebound of donor-specific antibodies is not addressed by IdeS. The use of IVIg and rituximab after transplantation is believed to prevent, or reduce the likelihood of, rebound donor-specific antibody responses to some extent.

Administration of IdeS pre-transplant to highly sensitized patients appeared effective as a means to reduce or eliminate donor specific antibodies, a strategy that may possibly improve transplant rates for human leukocyte antigen incompatible patients.

Example 2 Follow Up of Patients Treated with IdeS for Desensitization and HLA Incompatible (HLAi) Kidney Transplantation To understand the results from patients desensitized and transplanted after treatment with IgG endopeptidase, IdeS, we studied the long-term follow up of patients in the U.S. cohort (subsequent to the study in Example 1).

Eligible patients were HS 18 to 70 years awaiting kidney transplantation. All patients exhibited extensive sensitization with a median cPRA of 95%. Acceptance criteria for HLA-incompatible organs included a negative CDC cross-match, a negative flow cytometry cross-match or a positive T- and B-cell flow cross-match about 250 channel shifts or less and usually DSA positive. Patients meeting these criteria were enrolled.

Figure 12:
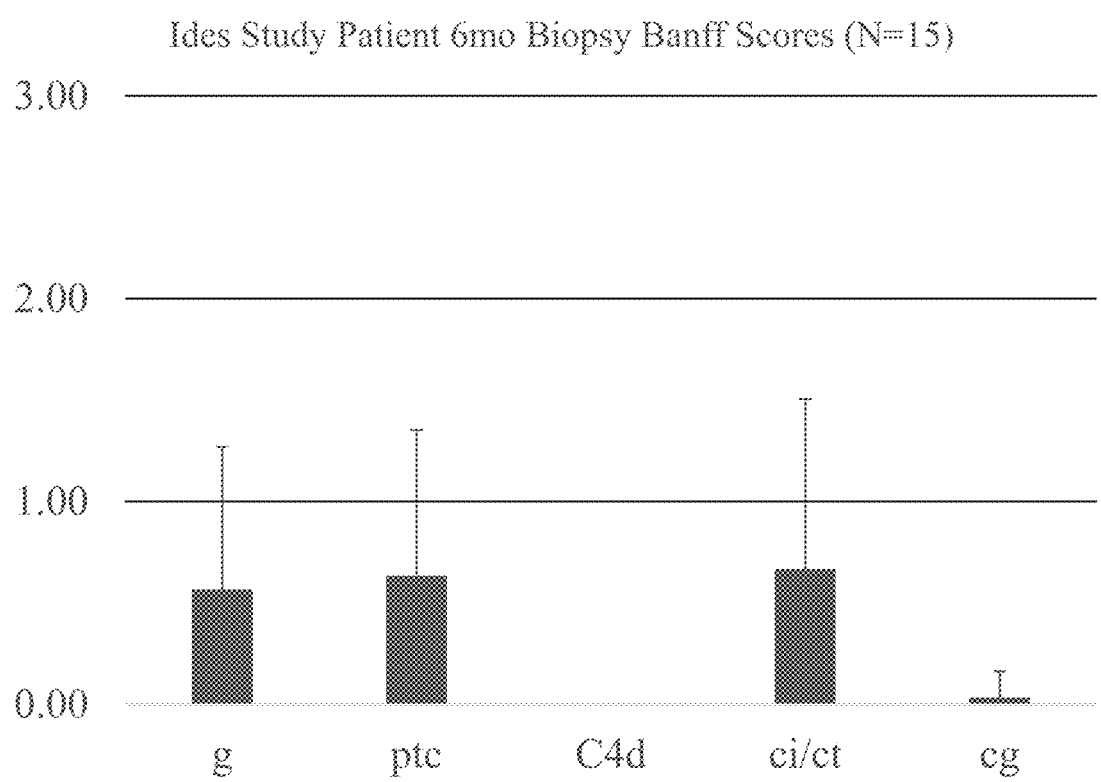
FIG. 12 depicts the Banff 2013 score of patient biopsies.

A total of 17 patients were transplanted from June 2015 to July 2017. Before and after transplantation desensitization included a combination of IVIg and an anti-CD20 agent. Data summarizing outcomes including the Banff biopsy scores, DSA levels and outcomes are shown in FIG. 12 and Table 3.

TABLE 3

Summary of long-term study (N = 17).

| Male/Female | 8 (47%)/9 (53%) |
|---|---|
| Ethnicity | |
| Caucasian | 4(23%) |
| Asian | 2(12%) |
| Hispanic | 10(59%) |
| Other | 1(6%) |
| Most recent average Cr (mg/dl) | 1.35 ± 0.92 |
| Most recent DSA (RIS$^+$ score) | 0.31 ± 0.60 |
| Number of patients with DSA to date | 4/17 (all weak MFI ≤3000) |
| Death Censored Graft Survival | 16/17 (94%)* |
| Patient Survival | 16/17 (94%) |

*1 patient had immediate transplant nephrectomy due to hyperIgM acute rejection.
$^+$Relative Intensity Score (RIS) defined as 0 points = No DSA; 1 point = 2500-3000 MFI; 2 points 3001-5000 MFI; 5 points = 5001-10,000 MFI; 10 points >10,000 MFI.

Graft and patient survival at a mean of 18.76±5.6 months after transplantation, desensitized with IdeS, were 94%. Rebound DSA responses were rare and of low MFI values with only 4 patients showing DSAs (all with MFIs≤3000). Biopsies were performed in 15 patients. All but three showed no or findings "suspicious" for ABMR that did not meet Banff criteria. No patient treated with IdeS had C4d+.

Therefore, patients desensitized with IdeS and transplanted with HLAi kidneys show good renal function and minimal evidence of allo-specific responses at mean 18.56 months after transplantation when a combination of IVIg and an anti-CD20 agent was administered both before and after transplantation.

The various methods and techniques described above provide a number of ways to carry out the application. Of course, it is to be understood that not necessarily all objectives or advantages described can be achieved in accordance with any particular embodiment described herein. Thus, for example, those skilled in the art will recognize that the methods can be performed in a manner that achieves or optimizes one advantage or group of advantages as taught herein without necessarily achieving other objectives or advantages as taught or suggested herein. A variety of alternatives are mentioned herein. It is to be understood that some preferred embodiments specifically include one, another, or several features, while others specifically exclude one, another, or several features, while still others mitigate a particular feature by inclusion of one, another, or several advantageous features.

Furthermore, the skilled artisan will recognize the applicability of various features from different embodiments. Similarly, the various elements, features and steps discussed above, as well as other known equivalents for each such element, feature or step, can be employed in various combinations by one of ordinary skill in this art to perform methods in accordance with the principles described herein. Among the various elements, features, and steps some will be specifically included and others specifically excluded in diverse embodiments.

Although the application has been disclosed in the context of certain embodiments and examples, it will be understood by those skilled in the art that the embodiments of the application extend beyond the specifically disclosed embodiments to other alternative embodiments and/or uses and modifications and equivalents thereof.

Preferred embodiments of this application are described herein, including the best mode known to the inventors for carrying out the application. Variations on those preferred embodiments will become apparent to those of ordinary skill in the art upon reading the foregoing description. It is contemplated that skilled artisans can employ such variations as appropriate, and the application can be practiced otherwise than specifically described herein. Accordingly, many embodiments of this application include all modifications and equivalents of the subject matter recited in the claims appended hereto as permitted by applicable law. Moreover, any combination of the above-described elements in all possible variations thereof is encompassed by the application unless otherwise indicated herein or otherwise clearly contradicted by context.

All patents, patent applications, publications of patent applications, and other material, such as articles, books, specifications, publications, documents, things, and/or the like, referenced herein are hereby incorporated herein by this reference in their entirety for all purposes, excepting any prosecution file history associated with same, any of same that is inconsistent with or in conflict with the present document, or any of same that may have a limiting affect as to the broadest scope of the claims now or later associated with the present document. By way of example, should there be any inconsistency or conflict between the description, definition, and/or the use of a term associated with any of the incorporated material and that associated with the present document, the description, definition, and/or the use of the term in the present document shall prevail.

It is to be understood that the embodiments of the application disclosed herein are illustrative of the principles of the embodiments of the application. Other modifications that can be employed can be within the scope of the application. Thus, by way of example, but not of limitation, alternative configurations of the embodiments of the application can be utilized in accordance with the teachings herein. Accordingly, embodiments of the present application are not limited to that precisely as shown and described.

Various embodiments of the invention are described above in the Detailed Description. While these descriptions directly describe the above embodiments, it is understood that those skilled in the art may conceive modifications and/or variations to the specific embodiments shown and described herein. Any such modifications or variations that fall within the purview of this description are intended to be included therein as well. Unless specifically noted, it is the intention of the inventors that the words and phrases in the specification and claims be given the ordinary and accustomed meanings to those of ordinary skill in the applicable art(s).

The foregoing description of various embodiments of the invention known to the applicant at this time of filing the application has been presented and is intended for the purposes of illustration and description. The present description is not intended to be exhaustive nor limit the invention to the precise form disclosed and many modifications and variations are possible in the light of the above teachings. The embodiments described serve to explain the principles of the invention and its practical application and to enable others skilled in the art to utilize the invention in various embodiments and with various modifications as are suited to the particular use contemplated. Therefore, it is intended that the invention not be limited to the particular embodiments disclosed for carrying out the invention.

While particular embodiments of the present invention have been shown and described, it will be obvious to those skilled in the art that, based upon the teachings herein, changes and modifications may be made without departing from this invention and its broader aspects and, therefore, the appended claims are to encompass within their scope all such changes and modifications as are within the true spirit and scope of this invention.

The invention claimed is:

1. A method for post transplant treatment or inhibition of antibody-mediated rejection (ABMR) in a subject who has received an organ transplantation, the method consisting of:
   administering a therapeutically effective amount of intravenous immunoglobulin (IVIG) and an anti-CD20 agent in one or more pharmaceutical compositions to the subject who has received an organ transplantation, or
   administering a therapeutically effective amount of the IVIG, the anti-CD20 agent, and one or more of anti-thymocyte globulin, alemtuzumab, a glucocorticoid, mycophenolate mofetil, tacrolimus, and antibiotics, in one or more pharmaceutical compositions to the subject who has received the organ transplantation,
   wherein the anti-CD20 agent comprises rituximab, ofatumumab, obinutuzumab, tositumomab, ocaratuzumab, ocrelizumab, TRU-015, IMMU-106, or a combination thereof; and
   wherein, if the subject did not receive rituximab before the transplantation, the IVIG and the anti-CD20 agent are administered only between 3 days and 10 days after the transplantation, or the IVIG is administered only between 7 days and 14 days after the transplantation and the anti-CD20 agent is administered only between 14 days and 21 days after the transplantation, or
   wherein, if the subject received the rituximab before the transplantation, the IVIG and the anti-CD20 agent are administered only between 3 days and 10 days after the transplantation.

2. The method of claim 1, wherein the subject has undergone treatment for depletion of anti-human leukocyte antigen (HLA) donor-specific antibodies (DSA) before the organ transplantation.

3. The method of claim 2, wherein de novo DSAs are produced in the subject after the organ transplantation and before the administration of the IVIG and the anti-CD20 agent.

4. The method of claim 2, wherein the treatment for depletion of DSA is IVIG or immunoabsorption therapy.

5. The method of claim 1, wherein the organ is any of heart, liver, lungs, pancreas or intestines.

6. The method of claim 1, wherein the organ is a kidney.

7. The method of claim 1, wherein the anti-CD20 agent comprises rituximab.

8. The method of claim 1, wherein the anti-CD20 agent is ofatumumab, rituximab, obinutuzumab, ibritumomab or combinations thereof.

9. The method of claim 1, wherein the IVIG and the anti-CD20 agent are administered sequentially.

10. The method of claim 1, wherein the subject did not receive the rituximab before the transplantation, and the IVIG is administered only between 7 days and 14 days after the transplantation and the anti-CD20 agent is administered only between 14 days and 21 days after the transplantation.

11. The method of claim 1, wherein the anti-CD20 agent is administered at a dose of about 375 mg/m$^2$ of body surface area.

12. The method of claim 1, wherein the IVIG is administered at about 2 grams/kg, for a maximum of 140 grams, to the subject over two days.

13. The method of claim 1, wherein the subject having received the IVIG and the anti-CD20 agent post transplant has a lower amount of donor-specific antibody compared to a control subject who does not receive a post transplant administration of said anti-CD20 agent and said IVIG.

14. The method of claim 1, wherein the subject having received the IVIG and the anti-CD20 agent post-transplantation has not received an anti-CD20 agent before the transplantation.

15. The method of claim 1, consisting of administering the therapeutically effective amount of the IVIG and the anti-CD20 agent in one or more pharmaceutical compositions to the subject who has received the organ transplantation.

16. The method of claim 1, consisting of administering the therapeutically effective amount of the IVIG, the anti-CD20 agent, and the one or more of antithymocyte globulin, alemtuzumab, a glucocorticoid, mycophenolate mofetil, tacrolimus, and antibiotics, in one or more pharmaceutical compositions to the subject who has received the organ transplantation.

17. The method of claim 1, wherein the subject's levels of human leukocyte antigen (HLA) antibodies and donor-specific antibodies (DSAs) were undetectable after the organ transplantation and before the administration of the IVIG and the anti-CD20 agent.

18. The method of claim 1, wherein the anti-CD20 agent is administered at a dose between 1 mg/kg and 50 mg/kg for one or more doses.

19. A method for reducing and/or eliminating donor specific anti-human leukocyte antigen (HLA) antibodies in a subject that has undergone organ transplantation, the method consisting of administering to the subject a therapeutically effective amount of intravenous immunoglobulin (IVIG) and an anti-CD20 agent in one or more pharmaceutical compositions to the subject after the organ transplantation, or administering a therapeutically effective amount of the IVIG, the anti-CD20 agent, and one or more of antithymocyte globulin, alemtuzumab, a glucocorticoid, mycophenolate mofetil, tacrolimus, and antibiotics, in one or more pharmaceutical compositions to the subject after the organ transplantation, wherein the anti-CD20 agent comprises rituximab, ofatumumab, obinutuzumab, tositumomab, ocaratuzumab, ocrelizumab, TRU-015, IMMU-106, or a combination thereof; and wherein, if the subject did not receive rituximab before the transplantation, the IVIG and the anti-CD20 agent are administered only between 3 days and 10 days after the transplantation, or the IVIG is administered only between 7 days and 14 days after the transplantation and the anti-CD20 agent is administered only between 14 days and 21 days after the transplantation, or wherein, if the subject received the rituximab before the transplantation, the IVIG and the anti-CD20 agent are administered only between 3 days and 10 days after the transplantation.

20. A method for treating a human leukocyte antigen (HLA)-sensitized subject who has undergone an organ transplantation, the method consisting of administering to the subject a therapeutically effective amount of intravenous immunoglobulin (IVIG) and an anti-CD20 agent in one or more pharmaceutical compositions to the subject who has undergone the organ transplantation, or administering a therapeutically effective amount of the IVIG, the anti-CD20 agent, and one or more of antithymocyte globulin, alemtuzumab, a glucocorticoid, mycophenolate mofetil, tacrolimus, and antibiotics, in one or more pharmaceutical compositions to the subject who has undergone the organ transplantation, wherein the anti-CD20 agent comprises rituximab, ofatumumab, obinutuzumab, tositumomab, ocaratuzumab, ocrelizumab, TRU-015, IMMU-106, or a combination thereof; and wherein, if the subject did not receive rituximab before the transplantation, the IVIG and the anti-CD20 agent are administered only between 3 days and 10 days after the transplantation, or the IVIG is administered only between 7 days and 14 days after the transplantation and the anti-CD20 agent is administered only between 14 days and 21 days after the transplantation, or wherein, if the subject received the rituximab before the transplantation, the IVIG and the anti-CD20 agent are administered only between 3 days and 10 days after the transplantation.

* * * * *